(12) United States Patent
Hyde, Jr.

(10) Patent No.: US 6,599,321 B2
(45) Date of Patent: Jul. 29, 2003

(54) MAGNETIC ARRAY IMPLANT AND PROSTHESIS

(76) Inventor: Edward R. Hyde, Jr., 900 Pepper Tree La. #1523, Santa Clara, CA (US) 95051

( * ) Notice: Subject to any disclaimer, the term of this patent is extended or adjusted under 35 U.S.C. 154(b) by 47 days.

(21) Appl. No.: 09/849,379

(22) Filed: May 4, 2001

(65) Prior Publication Data

US 2002/0032484 A1 Mar. 14, 2002

Related U.S. Application Data

(63) Continuation-in-part of application No. 09/594,356, filed on Jun. 13, 2000, now Pat. No. 6,387,096.

(51) Int. Cl.$^7$ ................................................. A61F 2/30
(52) U.S. Cl. ............................................... 623/18.12
(58) Field of Search ........................... 623/16.11, 18.11, 623/18.12, 19.11, 20.11, 20.14, 22.11; 446/137; 148/101; 433/189

(56) References Cited

U.S. PATENT DOCUMENTS

| | | | |
|---|---|---|---|
| 3,820,534 A | 6/1974 | Kraus et al. ............... 128/82.1 |
| 4,024,588 A | 5/1977 | Janssen et al. |
| 4,029,091 A | 6/1977 | von Bezold et al. |
| 4,038,704 A | 8/1977 | Ring |
| 4,057,858 A | 11/1977 | Helfet |
| 4,079,469 A | 3/1978 | Wadsworth |
| 4,129,902 A | 12/1978 | Harmon |
| 4,195,367 A | 4/1980 | Kraus |
| 4,203,216 A | 5/1980 | Deguemp |
| 4,214,322 A | 7/1980 | Kraus |
| 4,216,548 A | 8/1980 | Kraus ........................... 3/1.91 |
| 4,224,695 A | 9/1980 | Grundei et al. |
| 4,332,037 A | 6/1982 | Esformes et al. |
| 4,462,596 A | * 7/1984 | Yamamoto ................... 273/239 |
| 4,547,912 A | 10/1985 | Sherva-Parker |
| 4,741,698 A | 5/1988 | Andrews |
| 4,743,264 A | 5/1988 | Sherva-Parker |
| 4,781,720 A | 11/1988 | Sherva-Parker |
| 4,813,961 A | 3/1989 | Sostegni |
| 4,871,310 A | 10/1989 | Vardimon |
| 4,906,189 A | 3/1990 | Knapp |
| 5,062,855 A | * 11/1991 | Rincoe ........................ 623/24 |
| 5,168,183 A | 12/1992 | Whitehead |
| 5,337,030 A | * 8/1994 | Mohler .................. 310/156.37 |
| 5,421,722 A | 6/1995 | Stemmann |
| 5,462,054 A | 10/1995 | Rapoport et al. |
| 5,507,835 A | 4/1996 | Jore |
| 5,595,563 A | 1/1997 | Moisdon |
| 5,611,689 A | 3/1997 | Stemmann |
| 5,693,054 A | 12/1997 | Durham et al. ............... 606/62 |
| 5,725,597 A | 3/1998 | Hwang |
| 5,879,386 A | 3/1999 | Jore |

(List continued on next page.)

OTHER PUBLICATIONS

*Dexter Magnetic Technologies Permanent Magnet Catalog*, Dexter Corporation, Magnetic Technolgies, 1998.

Primary Examiner—Kevin Shaver
Assistant Examiner—Michael B. Priddy
(74) Attorney, Agent, or Firm—Pennie & Edmonds LLP

(57) ABSTRACT

The present invention relates to apparatus and methods for stabilizing and or maintaining adjacent bone portions in predetermined desired relationships and for constraining one, two or three-dimensional motion and/or rotation of the adjacent bone portions. Prostheses according to the present invention include cooperating magnetic arrays, preferably with plural magnets generating composite magnetic fields with predetermined field characteristics. The predetermined field characteristics are selected to interact such that the magnetic arrays on opposing prosthetic components cooperate to urge the bone portions into predetermined desired relationship and to constrain relative motion between the adjacent bone portions in various dimensions, e.g., rotation, flexion and/or extension thereof. Such magnetic constraint permits absorption and/or release of stress generated by externally applied forces.

20 Claims, 31 Drawing Sheets

U.S. PATENT DOCUMENTS

| | | |
|---|---|---|
| 5,886,609 A | 3/1999 | Stelter |
| 5,894,181 A | 4/1999 | Imlach |
| 5,929,546 A | 7/1999 | Lambert |
| 5,959,383 A | 9/1999 | Winzen et al. |
| 5,959,520 A | 9/1999 | Stelter et al. |
| 5,969,452 A | 10/1999 | Halsey et al. |
| 5,986,372 A | 11/1999 | Joffe |
| 6,171,107 B1 * | 1/2001 | Milne .................. 433/189 |

* cited by examiner

MAGNETIC ARRAY IMPLANT AND PROSTHESIS

This is a continuation-in-part of application Ser. No. 09/594,356 filed Jun. 13, 2000, now U.S. Pat. No. 6,387,096.

FIELD OF THE INVENTION

The present invention relates to apparatus and methods for stabilizing and maintaining adjacent bone portions in predetermined desired relationships and constraining one, two or three-dimensional motion and/or rotation of the adjacent bone portions, in particular, utilizing specially configured interacting magnetic array.

BACKGROUND OF THE INVENTION

Orthopedics is a medical subspecialty that treats disorders of the human body related to bones, muscles, ligaments, tendons, and joints, with its current emphasis on the treatment of the bones and joints. The treatment of bone and joint disorders can be generally subclassified into categories including the treatment of bone fractures, joint instability, early stage arthritis, and end stage arthritis. Originally, the treatment of orthopedic conditions had mainly relied on casting and bracing. However, with the advent of new implantable materials and development of better joint replacement prostheses, orthopedics shifted its focus to become increasingly more of a surgical subspecialty. With improved materials, better engineering, and a better understanding of the human body, the practice of orthopedic medicine and biomechanical experimentation have made remarkable progress. The treatment of bone fractures and joint disorders has continually been refined to the present state-of-the-art. The last 40 years have shown a myriad of innovations that have concentrated specifically on developing static mechanical design characteristics and new implantable materials used for fracture treatment and in total joint arthroplasties. These static mechanical design characteristics have been directed to solutions for problems concerning wear, stability, and methods of fixation for the total joint arthroplasties. They have also been utilized to improve the current state of the art concerning fracture treatment.

There have been some attempts to develop applications that utilize nonmechanical forces to augment the treatment of particular orthopedic problems. For example, pulsating electromagnetic field has been used as an adjunct to stimulating bone healing. Biochemical and biomaterial means have been used to alter the milieu at fracture sites and in joints to aid healing and to decelerate disease processes. Others have attempted to utilize magnetic fields in treatment of bone and joint disorders as well. For example, U.S. Pat. No. 4,024,588 to Janssen, et al. describes artificial joints with magnets. U.S. Pat. No. 4,029,091 to Von Bezold et al. discloses a method of applying plates to fractured bones so as to allow limited motions of the bone fragments when subjected to an externally generated electromagnetic force. U.S. Pat. No. 4,322,037 to Esformes et al. suggests a elbow joint including mechanically interlocking joint components with the inclusion of a magnetic force on the joint. U.S. Pat. No. 5,595,563 to Moisdon discloses a method of repositioning body parts through magnetic induction generated by extracorporeal magnetic or electromagnetic devices. U.S. Pat. No. 5,879,386 to Jore describes an apparatus to hold bones apart which can also be adjustable from inside the joint, possibly through arthroscopic means. The disclosed devices and methods had only limited uses for specific orthopedic problems. However, these designs are generally not practically feasible due to errors or misconceptions related to the practical application of orthopedic surgical treatments or, more importantly, a lack of understanding concerning the properties of permanent magnets in relationship to the mechanical environment found in the human body, especially as they relate to the normal functions of bones and joints. Accordingly, there remains a need in the art for improved apparatus and methods for less invasively locating and restraining bones in treatment of orthopedic conditions.

SUMMARY OF THE INVENTION

The present invention generally relates to apparatus and methods for controlling forces at adjacent bone portions and/or constraining motion of the adjacent bone portions in one or more dimensions. More particularly, the present invention relates to a magnetic apparatus with at least two magnetic arrays each of which is constructed and implanted in a predetermined manner and generates interacting magnetic fields. Once implanted and secured to the adjacent bone portions, the apparatus provides interacting magnetic fields in the vicinity of the adjacent bone portions and is capable of transducing magnetic energy into mechanical energy and mechanical energy into potential magnetic energy, thereby reproducing functionally anatomic and or anatomically advantageous positions of the bone portions.

An apparatus for treating adjacent bone portions according to the invention includes first and second magnetic arrays. The first magnetic array is configured and dimensioned to be secured to a first adjacent bone portion and to provide a first magnetic field having first predetermined field characteristics and the second magnetic array is configured and dimensioned to be secured to a second adjacent bone portion and to provide a second magnetic field having second predetermined field characteristics. The first and second predetermined field characteristics are selected to interact such that the magnetic arrays cooperate to urge the adjacent bone portions into the predetermined desired relationship and constrain relative motion between the bone portions in at least two dimensions. Preferably, one or both magnetic array may comprise multiple magnets to provide a composite magnetic field, which may be symmetrical or asymmetrical. In one preferred embodiment, interaction between the first and second magnetic fields urges the arrays into a predetermined relationship with a defined reference point confined within a boundary defined by the magnetic field of one of the magnetic arrays.

According to a further aspect of the invention, the first predetermined field characteristics comprise magnetic equipotential surfaces or lines forming at least two first peaks defining a valley therebetween and the second predetermined field characteristics comprise magnetic equipotential surfaces or lines forming at least one second peak. Preferably, the peaks and valleys are three dimensional, for example at least two first peaks and valley therebetween being defined by a three dimensional, rotated sinusoid, and at least one second peak being defined by a three dimensional paraboloid. The first and second magnetic arrays are then positioned with respect to each other such that the second peak is received between the at least two first peaks. In other words, the field of one array preferably penetrates the field of the opposite array. In this embodiment the second peak is received within, e.g., the annulus of the toroid which may be topologically described as a cup-shaped region generated by rotating a sinusoid about its vertical axis. Alternatively, the first magnetic array is configured and dimensioned to provide the predetermined field characteristics with magnetic flux lines such that at least two peaks have different magnitudes.

In a further alternative embodiment, the apparatus according to the invention also comprises a first magnetic array and at least a second magnetic array. Further arrays may be provided. In this embodiment, the first array includes at least two magnets, configured and dimensioned to be secured to a first adjacent bone portion and to provide a first, composite magnetic field having first predetermined field characteristics such as magnetic flux lines defining at least one region of first magnetic intensity bounded by one or more regions of second magnetic intensity. The second magnetic array is configured and dimensioned to be secured to a second adjacent bone portion and to provide a second magnetic field having second predetermined field characteristics such as magnetic equipotential lines defining at least one region of third magnetic intensity. The regions of different magnetic intensity interact to urge the adjacent bone portions into the predetermined desired relationship and constrain relative motion between the bone portions in at least two dimensions. According to various alternatives, the regions of second and third magnetic intensity may have approximately the same magnetic intensity or the regions of second and third magnetic intensity may have different magnetic intensities and the regions of first and second magnetic intensity may have opposite polarities or the regions of first and second magnetic intensity may have the same polarity.

In a further alternative embodiment, the first and second magnetic arrays are secured to the adjacent bone portions at a predetermined distance apart along a first axis, and are oriented with respect to each other in a predetermined relationship along at least a second axis orthogonal to the first axis. The second magnetic array includes at least one magnet. At least two magnets of the first array and at least one magnet of the second array are arranged with common poles in opposition to produce a predetermined repulsive force therebetween at the predetermined distance. Relative movement between the arrays along the second axis away from the predetermined relationship is resisted by interaction between the magnetic fields in the regions of second and third intensity.

In a further aspect of the invention, each array has an opposing face and a back face, and comprises at least two magnets, each magnet having a polar axis. The magnets of each array are aligned with their polar axes substantially parallel such that the poles of each magnet are adjacent and disposed at the faces of each array. The arrays thus may be adapted to be secured to adjacent bone portions opposite to each other with the opposing faces facing together and in a predetermined positions with respect to each other along a first axis substantially parallel to the polar axes and along at least a second axis substantially orthogonal to the polar axes. In one alternative embodiment, the magnets of each array are aligned with opposite poles positioned on the opposing faces and the predetermined position along the first axis comprises the first and second array being at least substantially in contact along the opposing faces. In this embodiment, interaction between the magnetic fields resists relative rotation between the arrays. In another alternative, the magnets of each array are aligned with the same poles positioned on the opposing faces and the predetermined distance along the first axis comprises a predetermined spacing. In this alternative embodiment, interaction between the magnetic fields resists reduction of the predetermined spacing and resists movement away from the predetermined position along the second axis while permitting rotation thereabout or about other axes positioned adjacent to the second axis. Moreover, in this latter embodiment, at least one the magnetic arrays may further comprise at least one magnet disposed in the array with an opposite pole positioned on the opposing face.

In a method for treating adjacent bone portions according to the invention, first and second magnetic arrays are secured to adjacent bone portions, each array being configured and dimensioned to provide a magnetic field having predetermined field characteristics. The arrays are positioned in a desired relationship. Relative motion of the adjacent bone portions is constrained in at least two dimensions, maintaining the desired relationship through interaction of the first and second magnetic fields. An alternative method according to the invention involves securing a first magnetic array to a first adjacent bone portion to provide a first composite magnetic field therearound, securing a second magnetic array to a second adjacent bone portion to provide a second composite magnetic field therearound, and disposing the first and second magnetic arrays in opposition to each other to simultaneously generate both repulsive and attractive force therebetween, thereby urging the adjacent bone portions into a predetermined desired relationship and constraining relative motion of the adjacent bone portions in at least two dimensions. In a further aspect of the invention, the first and second adjacent bone portions form opposing bone portions of an articular joint and wherein the magnetic fields interact to reduce the joint reactive forces while constraining the bone portions to move in a natural joint motion. In an alternative aspect of the invention, the first and second adjacent bone portions are opposite sides of a bone fracture and the magnetic fields interact to reduce and stabilize the fracture fragments.

According to further aspects of the invention, a magnetic array may be constructed by arranging one or more magnets or arranging the poles of the magnets (both collectively referred to as "magnets" hereinafter) in a predetermined configuration and/or orientation. Due to the coincidence of the magnetic fields of individual adjacent magnets, the magnetic array creates a composite magnetic field which is capable of exerting two- or three-dimensional magnetic force upon objects disposed nearby. By manipulating properties, shapes, and other characteristics of each magnet and by arranging them in a predetermined configuration and/or orientation, the magnetic arrays and their interaction can be utilized to control forces between the adjacent objects and/or constrain their motion in two or three dimensions including rotation.

In another aspect of the invention, the magnets of the magnetic array may be secured into a housing, while maintaining the configuration and/or orientation thereof. By providing prearranged configuration and/or orientation thereto, the magnetic array can be readily adapted to treat variety of orthopedic conditions. This arrangement avoids potentially unpredictable implantation of individual magnets into different locations in the adjacent bone portions, simplifies the implantation procedure, reduces the time of the surgical procedure, minimizes complications following the surgery, facilitates the healing process, and provides a treatment option that is easier to perform and can be performed in a competent fashion by a greater number of surgeons.

In yet another aspect of the invention, the magnetic arrays are implanted into adjacent bone portions so as to control forces at the adjacent bone portions and/or to constrain the motion of adjacent bone portions in one or more dimensions. When one magnetic array is disposed in an opposed relationship to another magnetic array, the composite magnetic fields of each of the magnetic arrays interact with each other, and generate dynamically interacting magnetic fields between and/or around those magnetic arrays. Characteristics of the interacting magnetic fields can be specifically controlled by manipulating properties, shapes, and/or other characteristics of each individual magnet in each magnetic array, because the resultant of the interacting magnetic fields is a vector sum of the individual composite magnetic fields of each magnetic array. By manipulating the repulsive and/or attractive forces generated therebetween, the magnetic arrays can provide potential energy to do work along the axis parallel and orthogonal to the direction of the magnetic polarity, as well as provide rotational stability for particular array designs to the adjacent bone portions. This potential energy can be used to reduce the reactive force between the bone portions, and/or limit motion between the bone portions. According to the invention, the orthopedic magnetic apparatus including the foregoing magnetic arrays may be applied to various orthopedic conditions such as long bone fractures, carpal bone fractures, joint instability, early arthritis and end stage arthritis. They may also be used to augment the designs of other total joint components. In treating fractures, the magnetic arrays of the invention may be arranged to create dominant attractive force, thereby providing the structural and/or rotational stability thereto.

As indicated, in one aspect of orthopedic application of the present invention, the magnetic arrays described herein above may be applied to treat degenerative conditions such as arthritis. For such degenerative conditions, the magnetic arrays may preferably be arranged to create dominant repulsive force, thereby providing potential magnetic energy to counteract mechanical forces along the axis parallel to composite magnetic force vector and provide stability along the axis orthogonal to the composite magnetic force vector. Benefits may be realized in reducing mechanical contact between the intact cartilage of the bone portions at a joint by reducing the joint reactive force and providing the additional means of control to diminish joint instability and/or the progression of joint disease. Moreover, the invention may be employed in or with prostheses to reduce the mechanical contact and the damage caused by friction between implanted prosthetic components, reducing joint reactive force, and providing the stabilizing capability, thereby decreasing pain associated with the end-stage arthritis and/or extending the functional life of the implanted components.

In a further aspect of the present invention, a magnetic orthopedic prosthesis may be provided to treat adjacent bone portions of a joint. Such prosthesis typically includes a first component capable of being secured to a first adjacent bone portion and including at least one first magnetic array providing a first magnetic field having first predetermined field characteristics, a second component capable of being secured to a second adjacent bone portion and including at least one second magnetic array providing a second magnetic field having second predetermined field characteristics, and at least one third component arranged to be movably disposed between the first and second components and including at least two third magnetic arrays disposed on different sides of the third component. Third magnetic arrays provide identical or different third magnetic fields each having third predetermined field characteristics. The first, second, and third predetermined field characteristics are selected to interact such that the first, second, and third magnetic arrays cooperate to urge the adjacent bone portions into predetermined desired relationship and to constrain relative motion between the adjacent bone portions in at least two dimensions, e.g., rotation, flexion and/or extension thereof.

In the alternative, such prosthesis may include a first magnetic component capable of being secured to the first adjacent bone portion and including at least one first magnetic array providing a first magnetic field having first predetermined field characteristics, a second non-magnetic component arranged to be secured to a second adjacent bone portion of said joint, and at least one third component arranged to be movably disposed between the first and second components and including at least one third magnetic array providing a third magnetic field having third predetermined field characteristics. The first and third predetermined field characteristics are selected to interact such that the first and third magnetic arrays cooperate to urge the adjacent bone portions into predetermined desired relationship and to constrain relative motion between the adjacent bone portions in at least two dimensions.

The term "adjacent bone portions" generally refers to any bones or portions thereof which are disposed adjacent to each other. The "adjacent bone portions" or simply the "bone portions" may mean any bones or their portions positioned adjacent to each other, whether they are separate or functionally coupled with each other, and/or mechanically contacting each other due to anatomical reasons, non anatomic reasons and/or surgical treatments. For example, a tibia and fibula, a radius and ulna, and a femur, tibia, and fibula are a few representative pairs or groups of the bones anatomically disposed adjacent to each other; a femur and tibia, a humerus and ulna, and a humerus and scapula are exemplary bone pairs functionally coupled to each other through a knee joint, elbow joint, and shoulder joint, respectively; and a clavicle and sternum are the bones mechanically contacting each other. The "adjacent bone portions" may also include any two or more bone segments which are to be positioned adjacent to each other, and/or contacting each other. Examples of such bones may include any number of fractured segments of a bone(s) and/or joint(s).

The terms "equipotential line" and "equipotential surface" mean, respectively, any curvilinear two-dimensional line and three-dimensional surface, representing characteristics of a magnetic field generated around a magnet(s). The "equipotential surface" is perpendicular to magnetic fluxes emanating from the magnet and is drawn by connecting points of the same magnetic intensity on the magnetic fluxes. The "equipotential line" is obtained by taking a cross-section of the "equipotential surface" in a predetermined direction. Thus, the "equipotential line" is a subset of "equipotential surface" and also perpendicular to the magnetic fluxes in the predetermined direction. For easy of illustration and simplicity, both "equipotential line" and "equipotential surface" will be collectively referred to as "equipotential line" hereinafter. Accordingly, "peaks," "valleys," and "gaps" of the "equipotential lines" are inclusive of those depicted in the two-dimensional "equipotential lines" as well as those in the three-dimensional "equipotential surfaces."

Other features and advantages of the invention will be apparent from the following detailed description, and from the claims.

DETAILED DESCRIPTION OF THE INVENTION

The following description provides exemplary embodiments of orthopedic methods and apparatus according to the present invention. In particular, the description provides examples of magnetic arrays, orthopedic apparatus incorporating those magnetic arrays, and applications of such magnetic arrays and orthopedic apparatus to various orthopedic conditions such as fractures, joint instability, early stage arthritis, end stage arthritis and augmentation of total joint components. This list and the examples contained herein are merely illustrative, and not exhaustive.

Figure 1A:
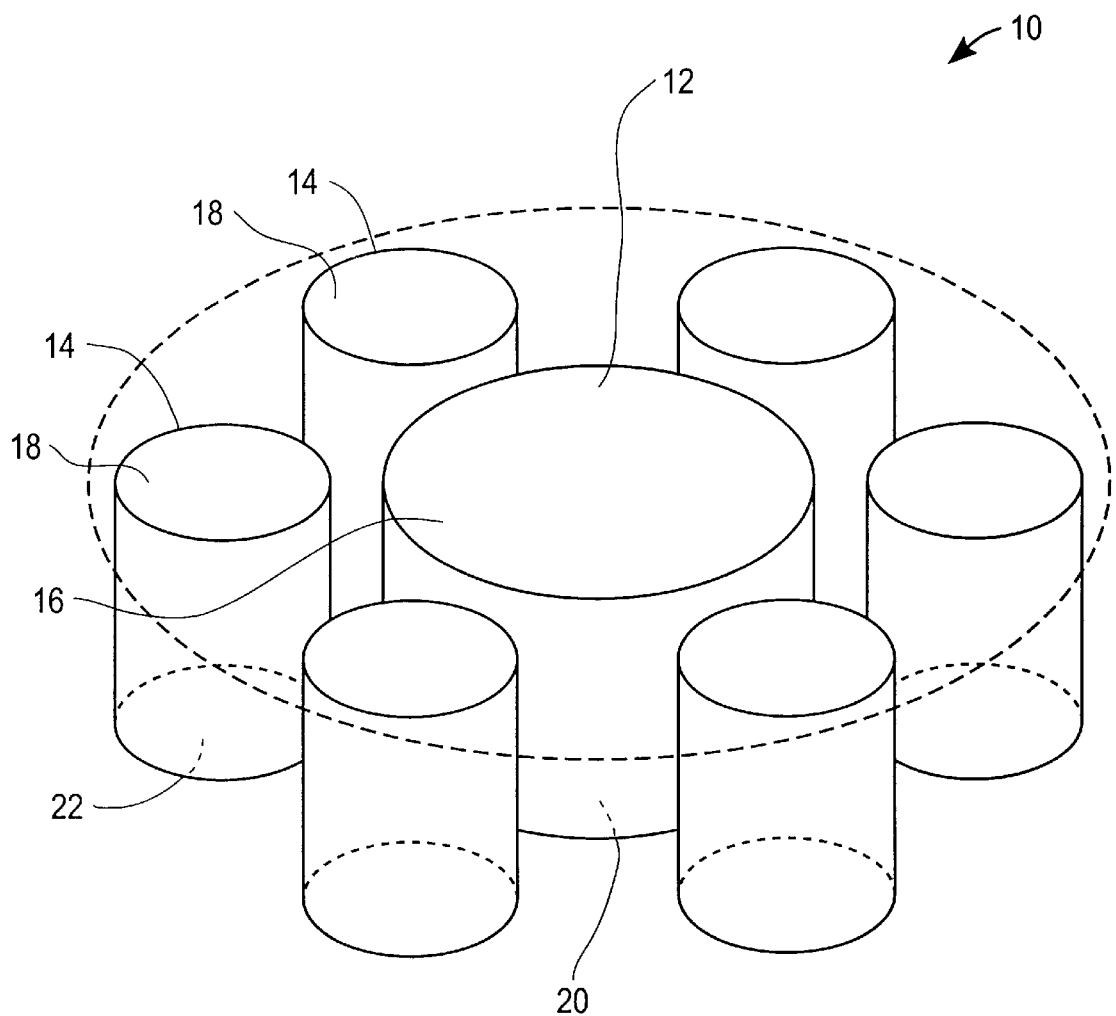
FIG. 1A is a perspective view of an example of a magnetic array with multiple magnets according to the present invention.
Figure 1B:
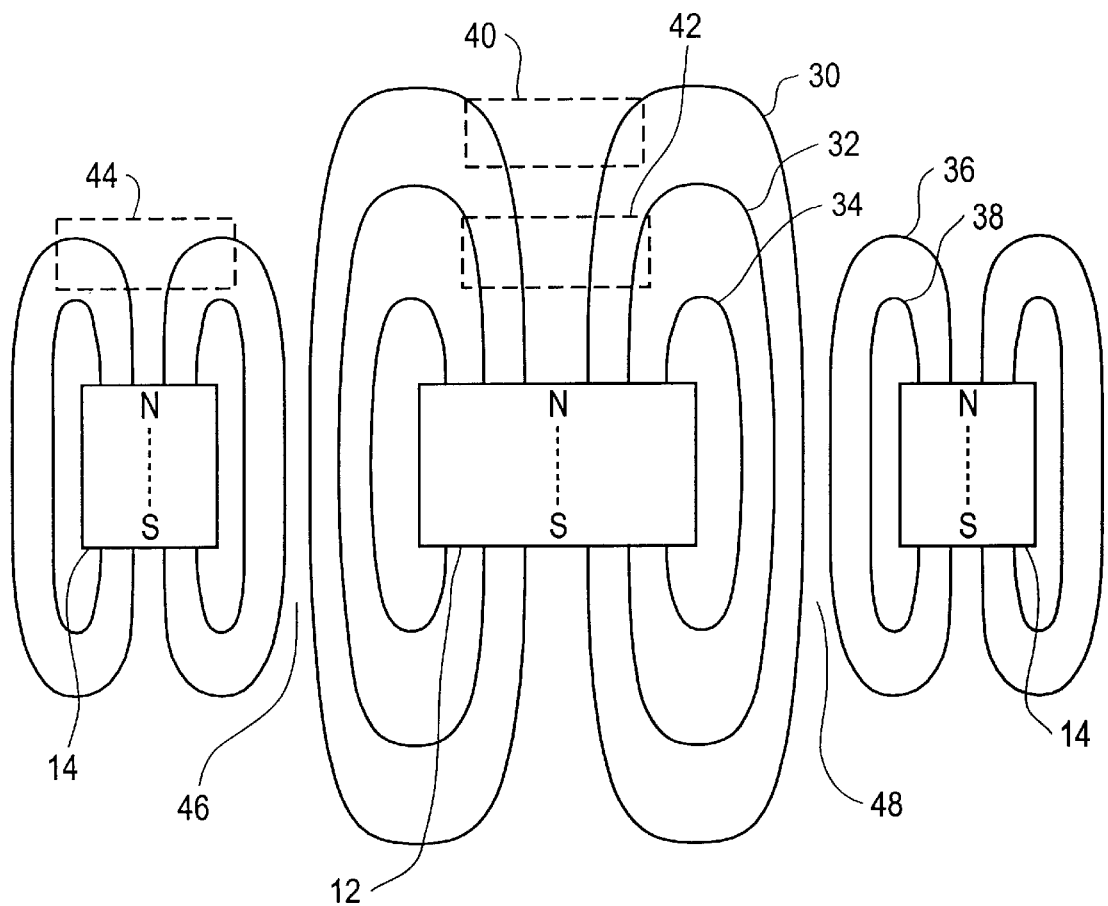
FIG. 1B is a cross-sectional schematic view of magnetic flux lines of a composite magnetic field generated around the magnetic array of FIG. 1A according to the present invention.
Figure 1C:
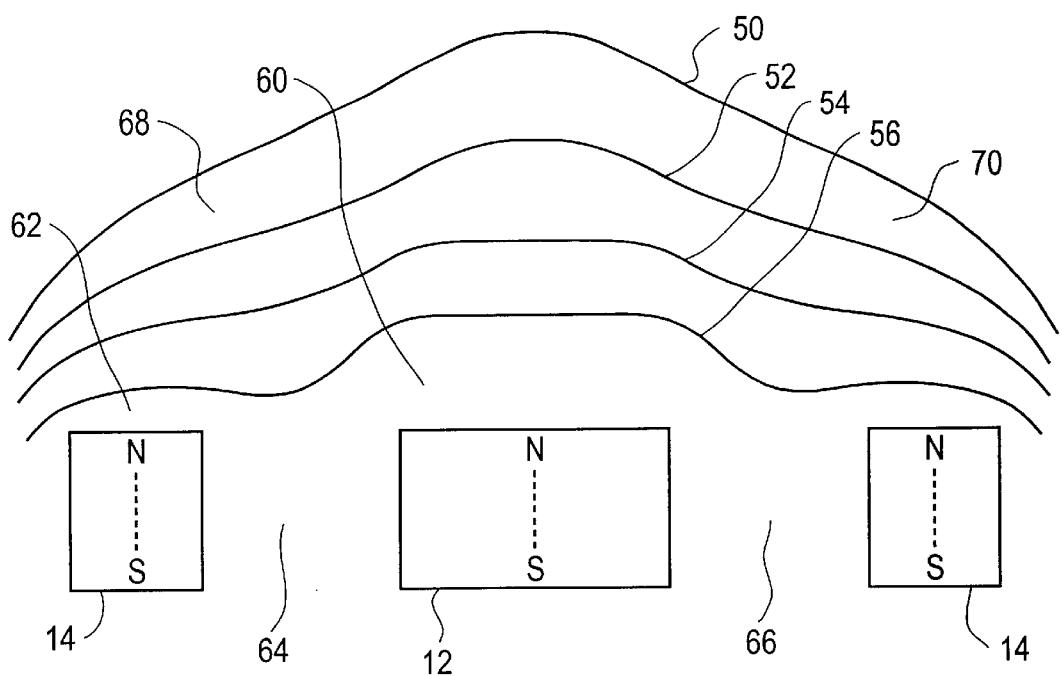
FIG. 1C is a cross-sectional schematic view of equipotential lines of a composite magnetic field generated around the magnetic array of FIG. 1A according to the present invention.

In one aspect of the invention, a magnetic array is provided by arranging one or more magnets in a specific configuration adapted to the particular application. FIGS. 1A, 1D, 1G, and 1I illustrate various embodiments of such magnets and magnetic arrays, while FIGS. 1B, 1C, 1E, 1F, and 1H illustrate characteristics of composite magnetic fields created by those magnetic arrays and their interactions. As shown in FIG. 1A, magnetic array 10 includes center magnet 12, which may be cylindrical, positioned at a center of a group of six peripheral magnets 14. In this embodiment all magnets 12, 14 are arranged with their north poles at their top faces 16, 18 and the south poles at their bottom faces 20, 22. The center magnet 12 may be selected to have greater "magnetic flux density" than the peripheral magnets 14 as schematically illustrated in FIGS. 1B and 1C. Note that references to orientation used herein, such as "top" and "bottom" or "above" and "below", are used only for clarity in discussing the figures and are not limiting of the invention described, which may be used in any orientation according to the teachings herein.

In alternative embodiments, different characteristics of the magnet design may be altered to provide the center magnet 12 with greater or lesser magnetic flux density. When all of the magnets in the array are made of the same material, their magnetic flux density can be increased by altering the placement, height, thickness or surface area of the magnet. Thus, center magnet 12 may differ from peripheral magnets 14 accordingly. Alternatively, center magnet 12 may be made of a different magnetic-energy material with a higher $(BH)^{max}$ such as any one of a range of NdFeB materials or any other magnetic material with appropriate flux density for the particular use, while peripheral magnets 14 are made of lower $(BH)^{max}$ material. Such a center magnet may be the same size or smaller than peripheral magnets 14. Regardless of the size or material, center magnet 12 may be fixed in the array at a level higher (or lower) with respect to the present surface than that of peripheral magnets 14. By positioning center magnet 12 at a higher (or lower) position relative to the other magnets in the array, the center magnet will contribute more (or less) to the composite magnetic field, affecting the object placed above (or below) magnetic array 10 to a greater or lesser extent.

FIG. 1B is a cross-sectional schematic view of magnetic flux lines of a composite magnetic field generated by the magnetic array of FIG. 1A according to the present invention. In FIG. 1B, magnetic flux lines 30, 32, 34 emanate from center magnet 12, whereas magnetic flux lines 36, 38 emanate from peripheral magnet 14. Because the magnetic axes (dotted lines drawn inside magnets to connect their opposite poles) of magnets 12, 14 are parallel to each other, the magnetic fields created by peripheral magnets 14 are generally parallel to the longitudinal axis of center magnet 12.

The magnetic flux lines may also be used to assess a spatial distribution pattern of magnetic intensity of the composite magnetic field of the magnetic array 10. For example, the magnetic intensity can be assessed in terms of "magnetic flux" which is defined as the amount of magnetic flux lines crossing a given area (such as those denoted by numerals 40, 42, 44). Alternatively, the magnetic flux may be calculated as an integral of a component of magnetic flux density perpendicular to the area divided by the area. Comparison of the magnetic flux densities crossing the areas 40 and 42 reveals that the magnetic intensity or magnetic flux decreases as the distance between magnet 12 and areas 40, 42 increases. In addition, magnetic flux lines 30–34 emanating from stronger center magnet 12 extend farther into the medium than flux lines 36, 38 emanating from weaker peripheral magnets 14. Because the same poles of the center and peripheral magnets are disposed on the same side of magnetic array 10, the center and peripheral magnets generate repulsive force acting against each other. Presence of such repulsive force is represented by annular zones 46, 48 formed between center and peripheral magnets 12, 14. It is appreciated that magnetic flux lines 30, 36 which emanate from different adjacent magnets but run in the same direction also delineate the existence of such repulsive force.

The spatial distribution pattern of the magnetic intensity (or flux) can also be assessed by mapping equipotential lines of force for the composite magnetic field. FIG. 1C is a cross-sectional schematic view of equipotential lines of the composite magnetic field generated around the magnetic array of FIG. 1A according to the present invention. Equipotential lines 50, 52, 54, 56 are curvilinear lines representing a vector sum of individual magnetic fields generated by center and peripheral magnets 12, 14. The equipotential lines are perpendicular to corresponding magnetic flux lines of the individual magnets 12, 14, and are drawn by connecting points of the same magnetic intensity on the magnetic flux lines. As illustrated in the FIG. 1C, the mapping of equipotential lines 50–56 facilitates the analysis of composite magnetic fields as well as provides a graphic representation of the characteristics of the composite magnetic fields. The map of equipotential lines 50–56 demonstrates that the contour of the equipotential lines depends not only on the specific characteristics of the magnets (i.e., material composition, size, shape, cross-sectional area, position, and orientation) but also on the distance from the magnet(s). FIG. 1C illustrates exemplary effects of distance on the contour of the equipotential lines. In the regions 60, 62, proximate to magnets 12 and 14, intensity (or flux) of the composite magnetic field is predominantly determined by that of the nearest magnet. Therefore, the contour of equipotential lines 54, 56 approximates the contour of the surface of the nearest magnet, which is manifest by the relatively flat profile of equipotential lines 54, 56 on or above magnets 12, 14. Transition zones are formed in gaps 64, 66 between magnets 12, 14 wherein equipotential lines 54, 56 form curves, the extent of which is generally proportional to the difference in the magnetic strengths between the neighboring magnets. In regions 68, 70, far away from magnets 12, 14, the intensity of the composite magnetic field generally decreases in proportion to a square of the distance from the magnet face. More importantly, however, the contour of equipotential lines 50, 52 becomes less dependent on the surface contour of the magnets. Rather, equipotential lines 50, 52 become smoother due to the summation of the weak magnetic fields of individual magnets 12 and 14.

Figure 1D:
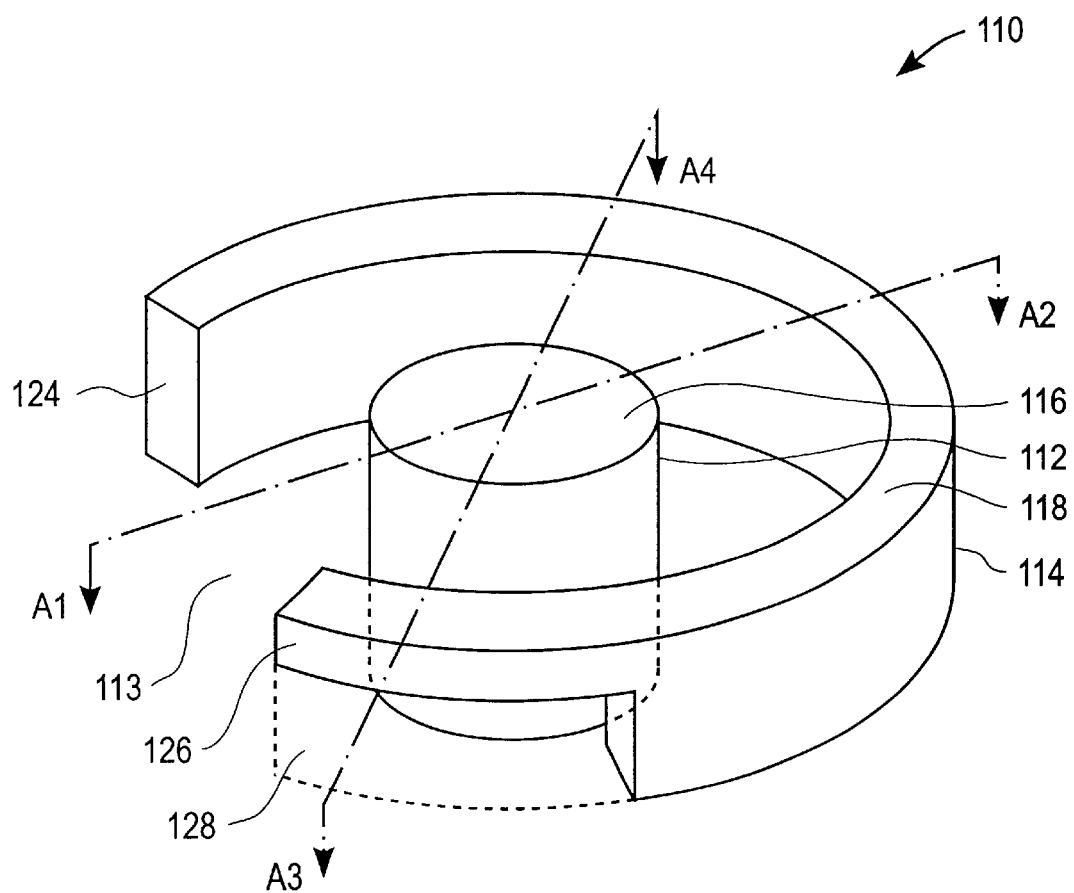
FIG. 1D is a perspective view of an alternative example of a magnetic array with multiple magnets arranged according to the present invention.

FIG. 1D is a perspective view of another embodiment of a magnetic array having multiple magnets arranged in a predetermined manner according to the present invention. Magnetic array 110 includes single C-shaped peripheral magnet 114 and cylindrical center magnet 112 disposed at a center of peripheral magnet 114. Peripheral magnet 114 is designed with a gap 113 between two ends 124, 126 so as to decrease the magnetic intensity thereanound. The lower portion 128 beside gap 113 is also truncated to decrease the magnetic intensity there above. Alternatively, gap 113 and/or lower truncated portion 128 may be filled with a material having magnetic properties which differ from those of peripheral magnet 114. Both magnets 112 and 114 are arranged to have the north poles on their top faces 116, 118 and the south poles on their bottom faces 120, 122 (shown in FIGS. 1E and 1F). Accordingly, the magnetic axes and longitudinal axes of magnets 112 and 114 are generally parallel to each other. As described herein above, center magnetic 112 is preferably designed to have greater magnetic flux density than peripheral magnet 114, e.g., by providing a larger center magnet 112, by making center magnet 112 of materials having greater magnetic energy, by positioning the center magnet at a level higher than that of the peripheral magnet or by configuring the center magnet to have a larger cross-sectional area. In many applications functional arrays are paired with one array having substantially the opposite configuration as the other array.

Figure 1E:
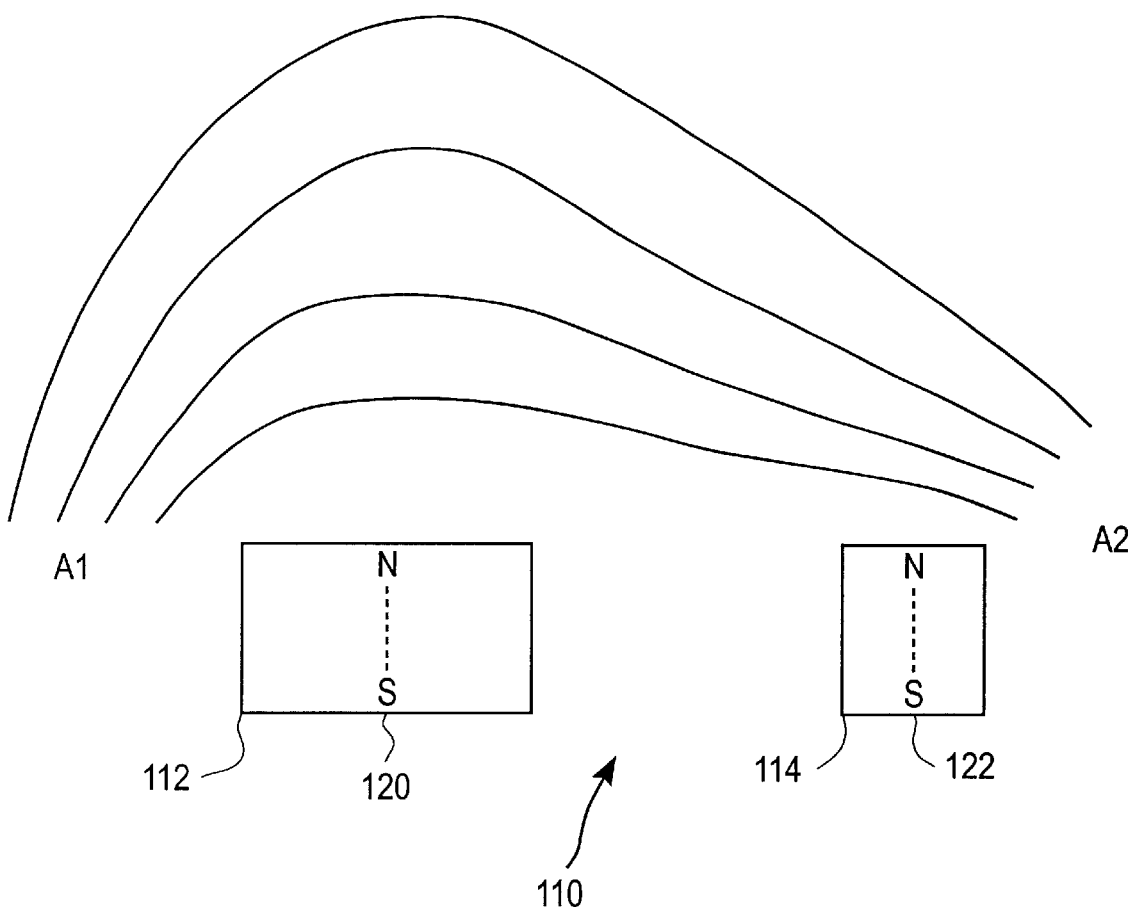
FIG. 1E is a cross-sectional schematic view of equipotential lines of a composite magnetic field through line A1-A2 of FIG. 1D according to the present invention.
Figure 1F:
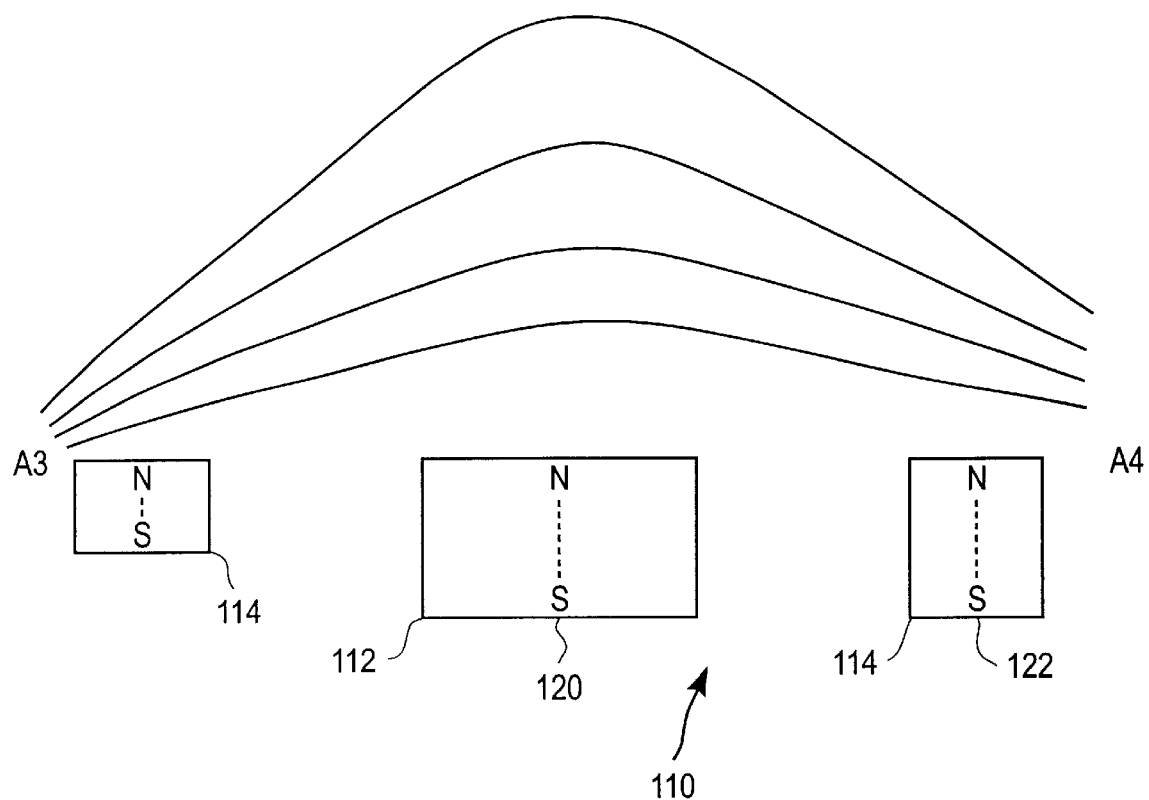
FIG. 1F is a cross-sectional schematic view of equipotential lines of a composite magnetic field through line A3-A4 of FIG. 1D according to the present invention.

FIG. 1E is a cross-sectional schematic view of equipotential lines of the composite magnetic field generated around the magnetic array of FIG. 1D according to the present invention, wherein the cross-section is taken through the array along the line A1-A2 of FIG. 1D. Because the line A1-A2 is drawn through gap 113 in the peripheral magnet 114, the magnetic field adjacent to gap 113 (or location A1) is substantially weaker than in the similar location on its opposite side (i.e., location A2). FIG. 1F is another cross-sectional schematic view of equipotential lines of the composite magnetic field generated around the magnetic array of FIG. 1D according to the present invention, wherein the cross-section is taken through the array along the line A3-A4 of FIG. 1D. Along the line A3-A4 drawn away from gap 113 of the peripheral magnet 114, the shapes of individual equipotential lines and the distribution pattern thereof are substantially similar to those of the magnetic array 100 described in FIGS. 1A to 1C, although the magnetic field above the truncated end 126 (or location A3) is weaker than its corresponding location on its opposite side (i.e., location A4). Accordingly, peripheral magnet 114 with the gap 113 and/or truncated portion 128 (or alternative material) generates an asymmetric magnetic field which in turn leads to create an asymmetric composite magnetic field for the entire array therearound. As will be discussed in greater detail below, this embodiment and others for asymmetric composite magnetic fields offer the benefit of constraining motion of above portion to a greater degree in one direction than another and at the same time allowing the comparative movement in one direction to be less constrained than in the other direction.

Figure 1G:
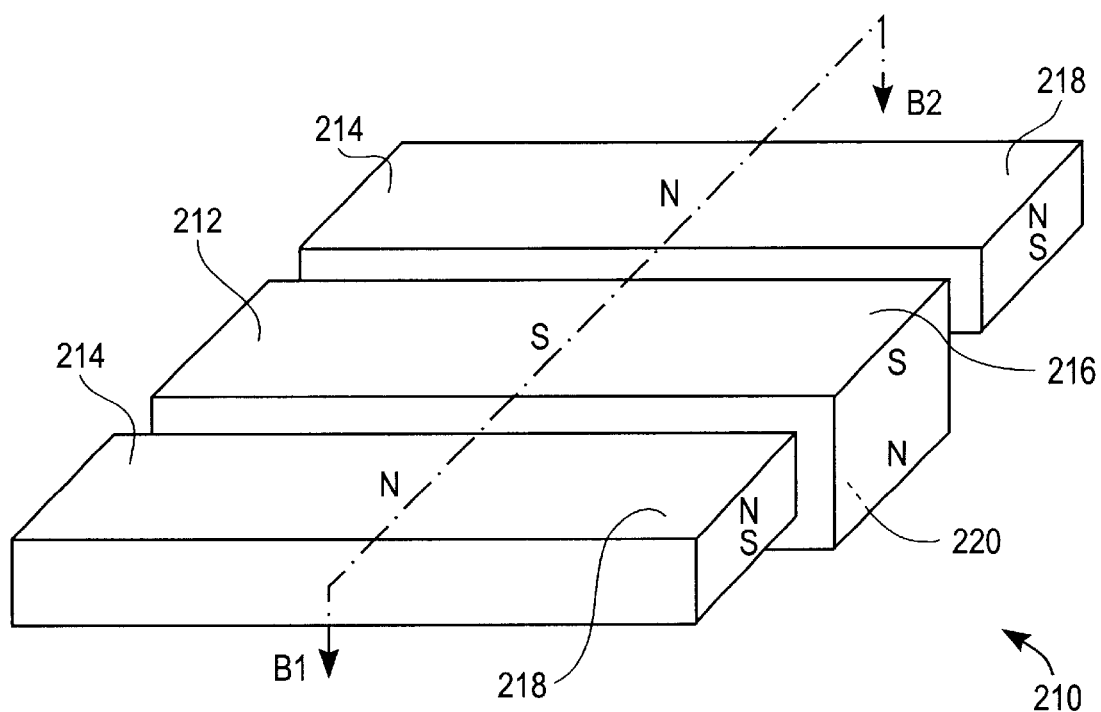
FIG. 1G is a perspective view of yet another magnetic array with multiple magnets arranged in a predetermined manner according to the present invention.

FIG. 1G is a perspective view of yet another magnetic array with multiple magnets arranged according to an alternative embodiment the present invention. Magnetic array 210 includes a rectangular center magnet 212 and two rectangular peripheral magnets 214 disposed on opposite sides of the center magnet 212. The south pole of center magnet 212 is positioned on top face 216 between the north poles of peripheral magnets 214. Similarly, the north pole of center magnet 212 is positioned on bottom face 220 between the south poles of peripheral magnets 214. Center magnet 212 may be arranged to have magnetic flux density greater than that of peripheral magnets 214, e.g., by making it thicker than peripheral magnet 214 as shown in the figure or by other methods described herein above. In addition, top faces 216, 218 of magnets 212, 214 are arranged to be flush with each other so as to provide magnetic array 210 with a flat upper surface.

Figure 1H:
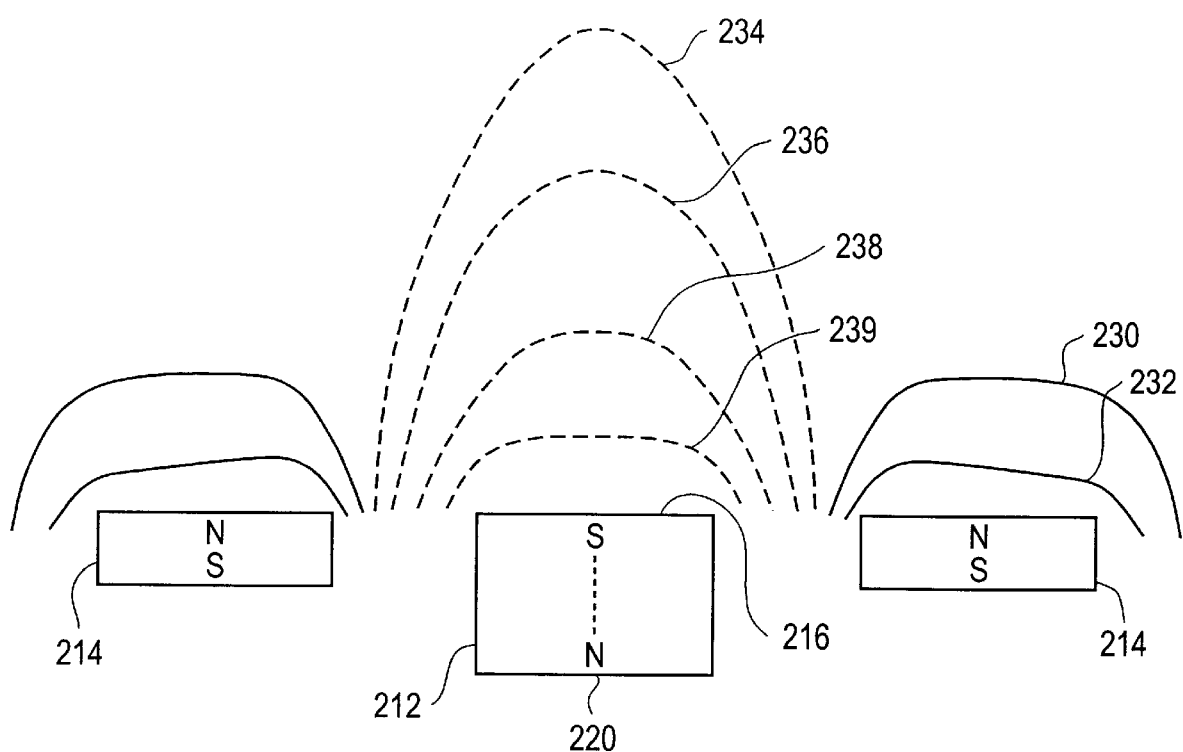
FIG. 1H is a cross-sectional schematic view of equipotential lines of a composite magnetic field through line B1-B2 of FIG. 1G according to the present invention.

FIG. 1H is a cross-sectional schematic view of equipotential lines of a composite magnetic field generated around the magnetic array of FIG. 1G according to the present invention, where the cross-section is taken along the line B1-B2 of FIG. 1G. Because the opposite poles are disposed adjacent to each other, presentation of the equipotential lines requires description of magnetic intensities having opposite polarities. Accordingly, solid lines 230, 232 are used to denote equipotential lines of magnetic fluxes emanating from the north poles of peripheral magnets 214, whereas broken lines 234, 236, 238, 239 are those emanating from the south pole of center magnet 212.

Figure 1I:
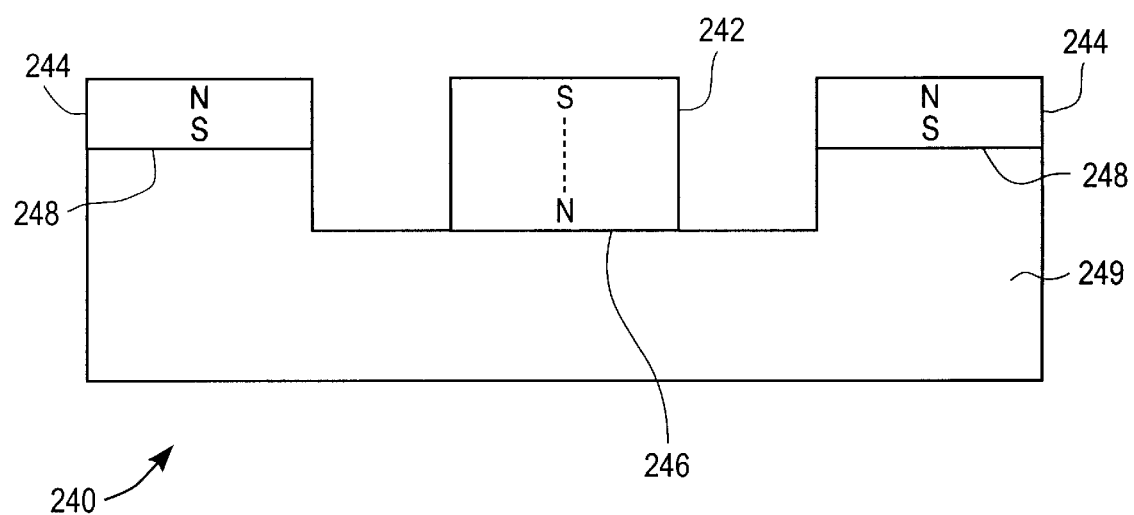
FIG. 1I is a cross-sectional schematic view of another alternative example of a magnetic array having a pole piece structure according to the present invention.

In general, magnetic arrays according to the invention are made of permanent magnets. Examples of such permanent magnets preferably include, but not limited to, rare earth cobalt magnets (e.g., samarium-cobalt, SmCo), and rare earth iron boron magnets (e.g., sintered neodymium-iron-boron, NdFeB). Magnetic arrays according to the invention may further include diamagnetic, paramagnetic, ferromagnetic, anti-ferromagnetic, and/or ferrimagnetic material, and/or any other materials that may be incorporated to affect or vary the configuration of the composite magnetic field created around the magnetic arrays. One example of such magnetic arrays is a pole piece where ferromagnetic material is placed at the north and/or south pole of one or more magnets so as to customize the magnetic field created around the magnetic array. Steel or other ferromagnetic material may be used to complete a circuit by contacting the magnets on their back surfaces. FIG. 1I is a cross-sectional schematic view of another alternative example of a magnetic array having a pole piece structure according to the present invention. Magnetic array 240 includes a center magnet 242 and peripheral magnets 244, wherein bottom faces 246, 248 of center and peripheral magnets 242, 244 are coupled to a ferromagnetic base 249. The center magnet may be cylindrical, positioned at a center of a group of peripheral magnets or inside a ring- or C-shaped peripheral magnet. Alternatively, the center and peripheral magnets may be rectangular, similar to those of FIGS. 1G and 1H. It is further appreciated that materials for the magnetic arrays may preferably have sufficient mechanical strength to survive the rigors and stresses of implantation and throughout the course of the orthopedic treatment.

It is appreciated that various factors may affect the contour of the equipotential lines. Examples of such factors may include, but not limited to, material, shape, size, polarity, magnetic strength, orientation, surface area and distribution pattern of the magnets. Further examples may also include embodiments where there are alterations in the orientation of the magnetic axis, the number and distribution pattern of poles on each side of the magnets, the presence of insulating or conductive material around or between the magnets, and the presence of symmetry or asymmetry of the magnets or magnetic arrays.

Figure 2A:
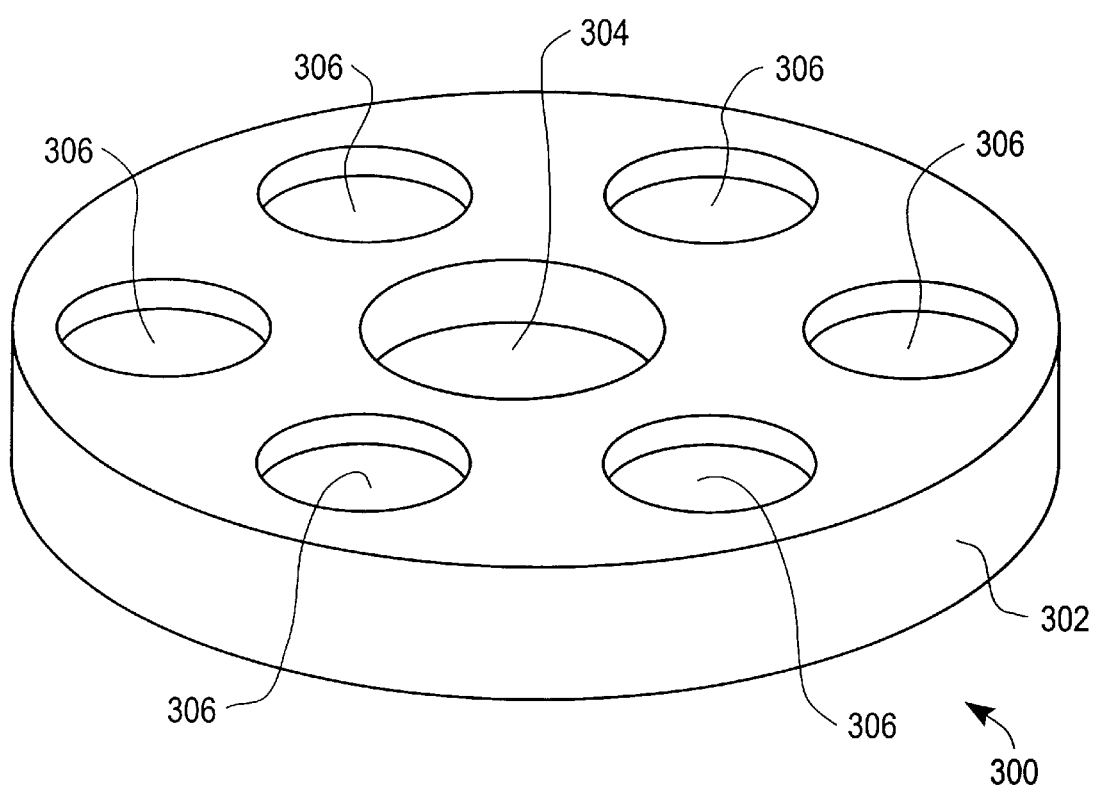
FIG. 2A is a perspective view of one embodiment of a housing for securing magnets of a magnetic array according to the present invention.
Figure 2B:
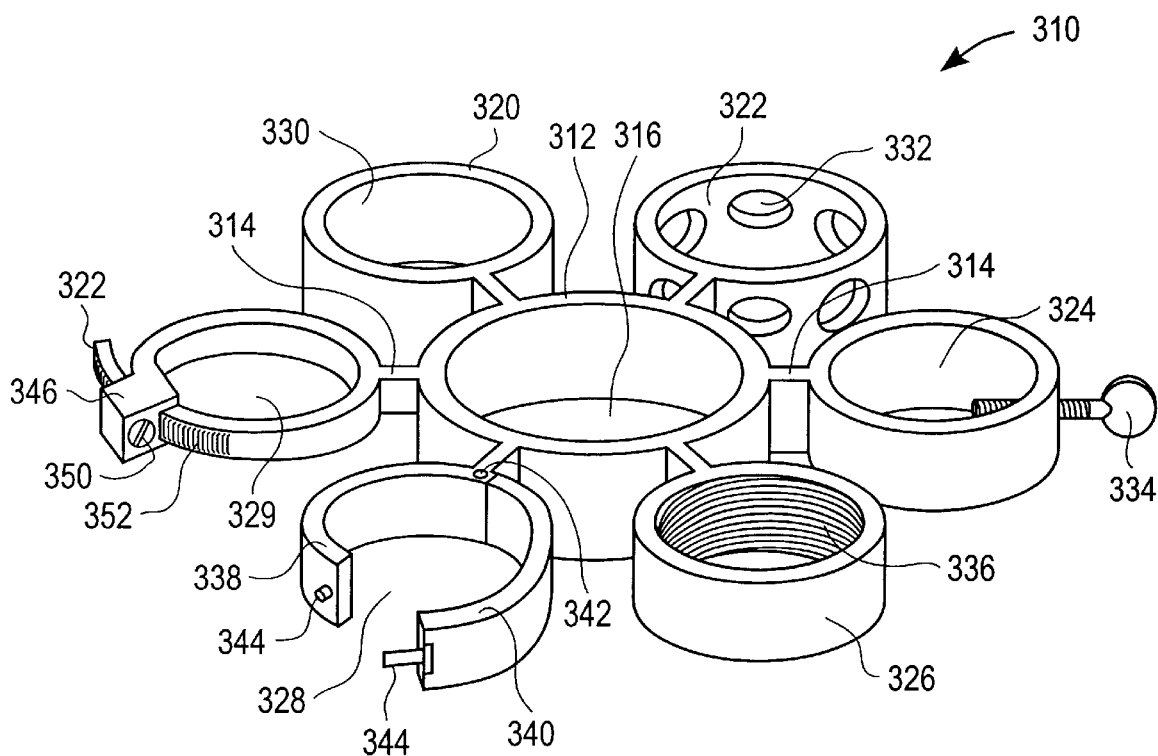
FIG. 2B is a perspective view of an alternate embodiment of a housing for securing magnets of a magnetic array according to the present invention.

In another aspect of the invention, the magnetic arrays may include a housing to support and secure the magnets of the array. Due to attractive or repulsive forces exerted by the magnets, the configuration of an unsecured magnetic array may deviate or be deformed from its predetermined arrangements as an individual unit. Accordingly, a housing may be shaped and sized to maintain the overall configuration or arrangement of the magnets and the orientation of each magnet with respect to the other ones. FIGS. 2A and 2B illustrate two exemplary embodiments for housings for the magnetic arrays.

FIG. 2A is a perspective view of a housing for securing magnets of the magnetic array of FIG. 1A according to an embodiment of the present invention. Housing 300 includes housing body 302 made of biocompatible or implantable polymers and/or other materials which will be described in greater detail below. Housing 300 also includes center receptacle 304 and multiple peripheral receptacles 306 disposed around center receptacle 304. Each receptacle forms a cavity shaped and sized to receive corresponding magnets. For example, receptacles 304, 306 may be arranged to have cavity diameters substantially equal to or slightly greater than the diameters of magnets 12, 14 of FIG. 1A, respectively. Each receptacle 304, 306 may be designed with a predetermined cavity depth such that only a predetermined portion or faces of magnets 12, 14 may be exposed after the assembly. Assembled magnets 12, 14 can be secured to housing body 302 by adhesives, a friction fit, an interference fit, threads, couplers, and/or other conventional coupling devices and methods known in the art.

It is appreciated that the shape and size of the receptacles do not have to conform precisely to those of the magnets. For example, receptacles may be arranged to receive magnets with different shapes and/or sizes by using, e.g., fillers, spacers, and/or other adaptors and couplers known in the art. Receptacles or magnets may also be designed to include additional size-independent coupling mechanisms known in the art, e.g., screws and latches. In addition, receptacles may be arranged to have standardized shape, size, and/or patterns. This embodiment offers a user the ability to customize the distribution pattern of the magnets of the magnetic array. Furthermore, magnets or receptacles may have adjustable insertion depth.

FIG. 2B is a perspective view of another housing for securing the magnets of the magnetic array of FIG. 1A according to the present invention. Housing 310 typically includes circular housing body 312 and multiple arms 314 disposed therearound. Housing body 312 defines center receptacle 316 arranged to receive a center magnet through its center cavity and to secure it thereto by a friction or interference fit. Multiple arms 314 extend from housing body 312 and include distal ends each of which terminates in at least one of multiple peripheral receptacles 320, 322, 324, 326, 328, 329. For example, first peripheral receptacle 320 receives a peripheral magnet through its cavity and secures the peripheral magnet thereto by a tapered inner wall 330. Second peripheral receptacle 322 also receives a peripheral magnet through its cavity but secures the peripheral magnet by auxiliary magnets (not shown) disposed in apertures 332 formed along a side wall of receptacle 322. Third peripheral receptacle 324 is arranged similarly to first receptacle 320, but secures a peripheral magnet thereto by a threaded hole and an interference screw 334 inserted therethrough. Fourth peripheral receptacle 326 includes threaded cavity wall 336 which receives a peripheral magnet having a threaded outer wall. Fifth peripheral receptacle 328 has stationary arm 338, movable arm 340 which is coupled to the receptacle 328 by a hinge 342, and latch 344 arranged to secure a peripheral magnet. Sixth peripheral receptacle 329 is provided with fastener 346 having screw 350 and threaded strip 352 engaged with screw 350. By rotating screw 350, threaded strip 352 may be fastened to secure a peripheral magnet therein. Other conventional securing mechanisms known in the art may also be used to secure peripheral magnets into housing 310.

The housing may be made of any conventional or hereafter conceived biocompatible or implantable materials. Examples of such materials may include, but not limited to, any biomedical grade polymers, non-corrosive metals, plastics and ceramics. It is appreciated that any non-biocompatible and corrosive materials may also be used to construct the housing as long as they are coated with a layer of or encased in a biocompatible or implantable material having an appropriate thickness. It is further appreciated that materials for the housing preferably have mechanical strength to survive the rigors and stresses of implantation and for the duration of the orthopedic treatment. The housing or at least a portion thereof may include magnetic, diamagnetic, paramagnetic, ferromagnetic, antiferromagnetic, and/or ferrimagnetic material, and/or any other materials that may affect or vary the configuration of the composite magnetic field created around the magnetic array. This embodiment offers the ability to custom design a magnetic array that generates the desired complex composite magnetic field therearound. The housing may also include a magnetic insulator or conductor disposed at appropriate locations. In particular, when the opposite poles of the magnets are disposed adjacent to each other, the insulator is provided between such magnets to minimize leakage of the magnetic field and unwanted interaction between those magnets. It is preferred that the magnet array be further coated with, incased by, embedded in or molded in biocompatible material for safety and ease of application. According to a further alternative embodiment described in greater detail below, the housing may comprise the components of a traditional implant.

In operation, magnets are provided to have suitable shape, size, polarity, and magnetic intensity. These magnets are positioned in the receptacles of the housing body according to predetermined distribution pattern, polarity, and orientation. Depending on the detailed configuration of the receptacles and distribution pattern thereof, a user may be allowed to customize the distribution pattern of the magnets, the orientation of each magnet with respect to the others, and the insertion depth of each magnet. Once the magnets are properly positioned on the housing, the magnets are secured to the housing by various conventional methods described herein above.

In another aspect of the invention, two or more magnetic arrays may be secured to the adjacent bone portions so as to stabilize the bone portions in a predetermined desired relationship and/or to constrain motion of the bone portions with respect to each other. If appropriate, the bone portions may be urged into proper relationship by the magnetic arrays. When one magnetic array is disposed adjacent to another magnetic array, composite magnetic fields of those magnetic arrays interact with each other, and generate a dynamic, interacting magnetic fields between or around the magnetic arrays. It is noted, however, that the characteristics of the interacting magnetic fields are determined by those of individual composite magnetic fields of each array and resultant force is obtained as a vector sum of the individual composite magnetic fields. FIGS. 3A to 3F illustrate exemplary embodiments of applications of such interacting magnetic fields.

Figure 3A:
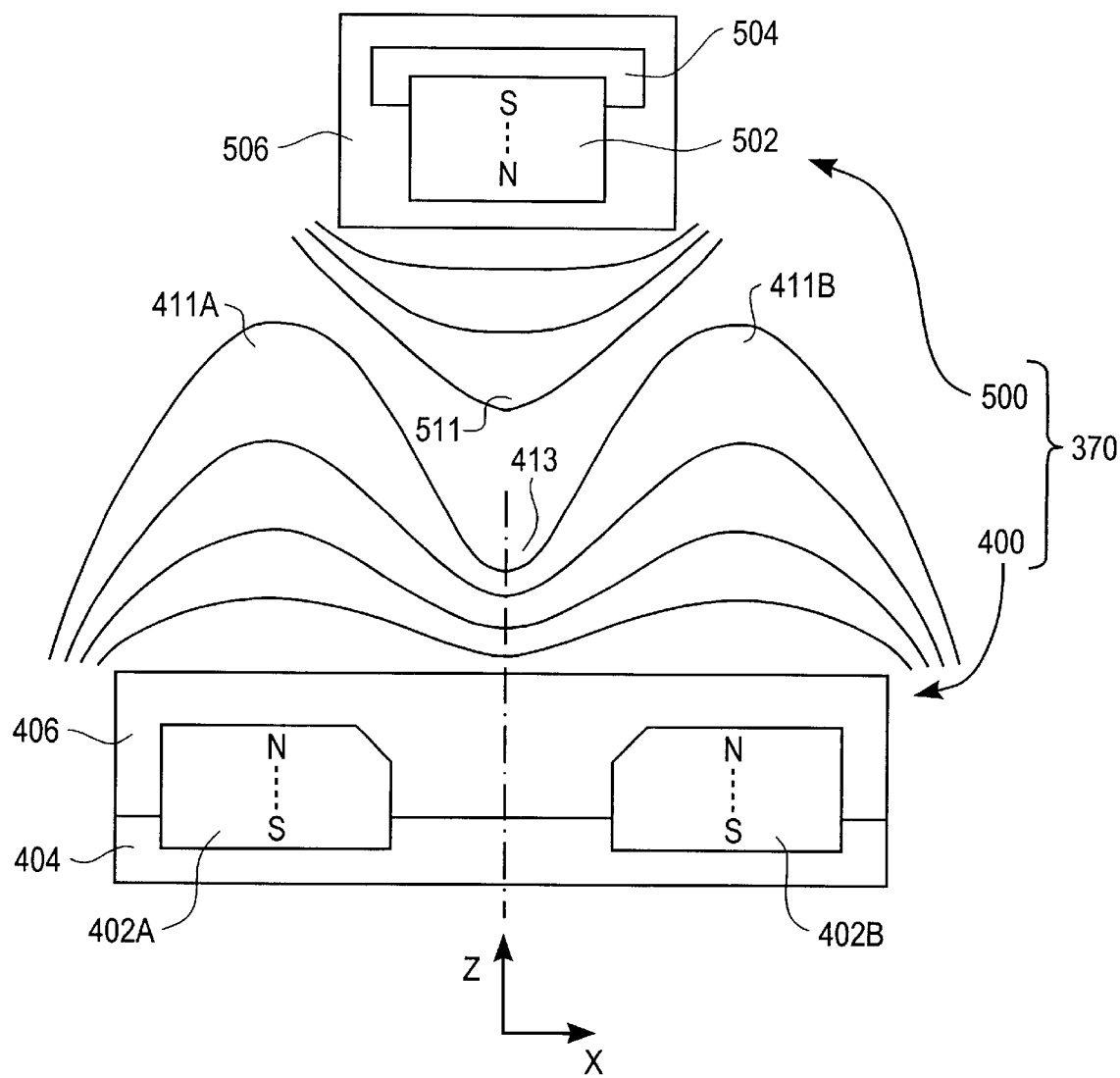
FIG. 3A is a cross-sectional schematic view of one embodiment of a magnetic apparatus for providing stabilizing magnetic field according to the present invention.

FIG. 3A is a cross-sectional schematic view of magnetic apparatus for providing stabilizing magnetic field according to the present invention. Exemplary magnetic apparatus 370 includes two magnetic arrays disposed adjacent to each other, i.e., first magnetic array 400 and second magnetic array 500 disposed opposite first magnetic array 400. First magnetic array 400 includes two magnets 402A, 402B secured to housing 404, with their upper faces flush with each other and their north poles facing upward. (Alternatively, magnets 402A, 402B may represent different cross-sectional portions of a single peripheral ring- or c-shaped magnet.) First magnetic array 400 may further include a cover 406 sealingly placed over magnets 402A, 402B and housing 404, thereby enclosing both magnets 402A, 402B and housing 404 therein. Because the same poles of magnets 402A, 402B are disposed on the same side, first magnetic array 400 generates a composite magnetic field where its equipotential lines form (in cross-section) two symmetric peaks 411A, 411B and a valley 413 therebetween. In three dimensions the magnetic field will have a cup-like, continuous, rotated sinusoidal shape. Second magnetic array 500 includes magnet 502 positioned on housing 504, with the same (north) pole oriented towards the opposing array. Both magnet 502 and housing 504 are encased inside an outer housing 506. Second magnetic array 500 generates a composite magnetic field with equipotential lines forming a single three dimensional peak 511 above the center portion of magnet 502.

When second magnetic array 500 is positioned above and adjacent to first magnetic array 400, with its north pole facing the north poles of the magnets in array 400, the composite magnetic fields of magnetic arrays 400 and 500 form dynamic interacting magnetic fields, wherein a "repulsive force" exerted between the two arrays 400, 500. Both the magnitude and the direction of this net repulsive force depend on the position of each magnetic array with respect to the other.

The embodiment of FIG. 3A offers the benefit of providing magnetic potential energy to the magnetic apparatus 370, i.e., it has potential to do work to offset any force that would cause one magnetic array to contact or increase the reactive force between it and the other array. For example, when a load is applied to second magnetic array 500 vertically (along the z-axis), the second array will tend to move vertically toward first magnetic array 400. As the magnitude of the load increases, the distance between the magnetic arrays will decrease, however, the repulsive force will at the same time increase in strength accordingly ($\sim 1/r^2$) such that the two arrays reach an equilibrium state (application of excessive force will cause the magnets to come in contact). When an axial load is removed or decreased, the potential energy of the interacting magnetic fields is converted back to the mechanical energy, repelling second magnetic array 500 away from first magnetic array 400 to a new equilibrium position. As will be discussed in greater detail below, designs according to the invention, such as magnetic apparatus 370, beneficially minimize frictional damage or destruction of the adjacent bone portions of joints.

Furthermore, apparatus according to the invention may be designed to deter radial displacement of one magnetic array away from its centralized equilibrium position with the opposite array. Arrangement of the magnetic arrays, as in FIG. 3A, also imparts a self-centering interactive force. Referring again to FIG. 3A, when second magnetic array 500 is moved horizontally along the x-axis, peak 511 of its composite magnetic field approaches one of the peaks 411A, 411B of the composite magnetic field of first magnetic array 400, e.g., peak 411B of magnet 402B. As the magnitude of the radial component of the load increases, the distance between the peaks 511, 411B will decrease and the radial component of the repulsive force will increase accordingly. The mechanical energy applied to magnetic apparatus 370 is converted to the potential energy of the interacting magnetic fields which will have skewed equipotential lines densely packed around the peaks 511, 411B. When the lateral load is removed or decreased, the potential energy of the interacting magnetic fields or at least a portion thereof is converted back to the mechanical energy by repelling second magnetic array 500 toward its centralized equilibrium position and returning the densely packed equipotential lines to their loosely packed state. As will be discussed in greater detail below, the radial stability provided by magnetic apparatus 370 may be applied to confine the motion of the adjacent joint bone portions to a predetermined range, thereby restricting out-of-range displacement thereof.

It will be appreciated by persons skilled in the art that magnetic arrays with different embodiments may also provide above described axial and/or radial stability. For example, the magnetic apparatus may have a first magnetic array having a center magnet and an annular peripheral magnet disposed therearound, wherein the peripheral magnet has greater magnetic intensity than the center magnet. The second magnetic array may be constructed substantially similar to the embodiment of FIG. 3A or may include a center magnet and an annular peripheral magnet disposed therearound, where the center magnet has greater magnetic intensity than the peripheral one. In the alternative, one array may include a weaker center magnet and multiple peripheral magnet disposed around the center magnet. In addition, the magnetic apparatus may also include magnetic arrays forming more than two peaks and/or more than one valley.

Figure 3B:
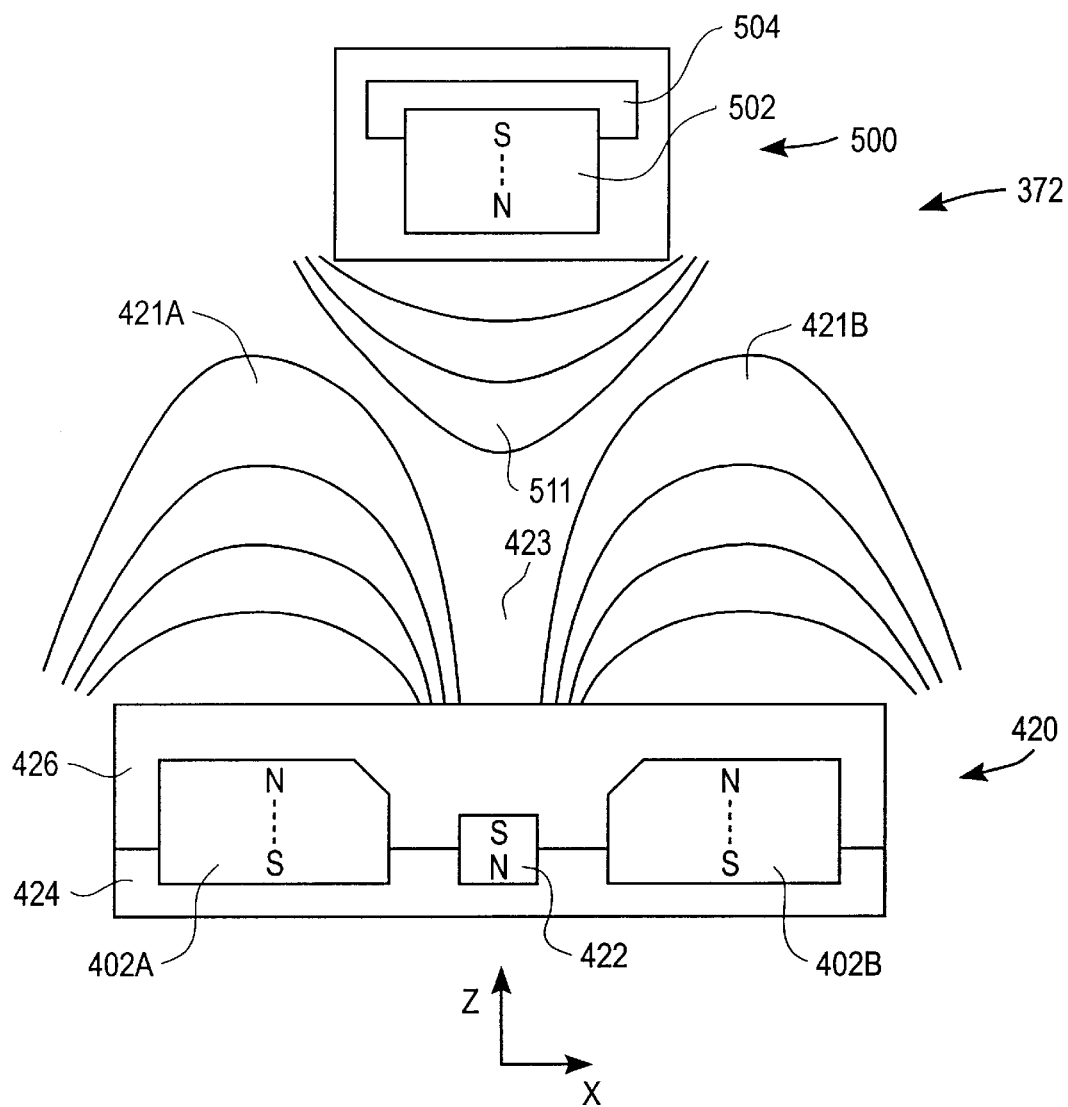
FIG. 3B is a cross-sectional schematic view of another magnetic apparatus for providing stabilizing magnetic field according to an alternate embodiment of the present invention.
Figure 3C:
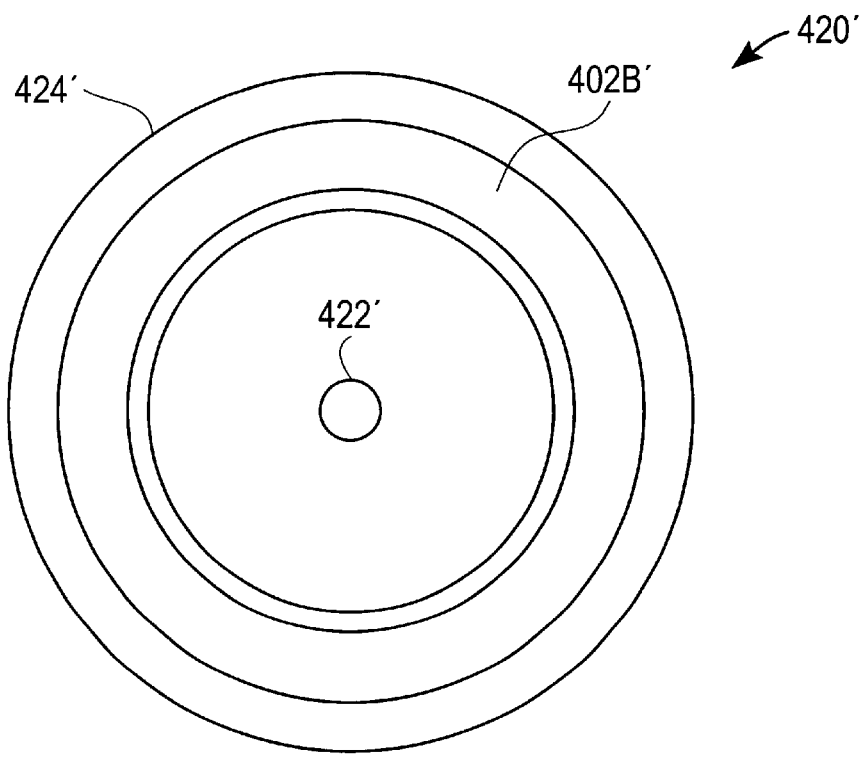
FIGS. 3C and 3D are plan views of alternative embodiments of the array as shown in cross-section in FIG. 3B.
Figure 3D:
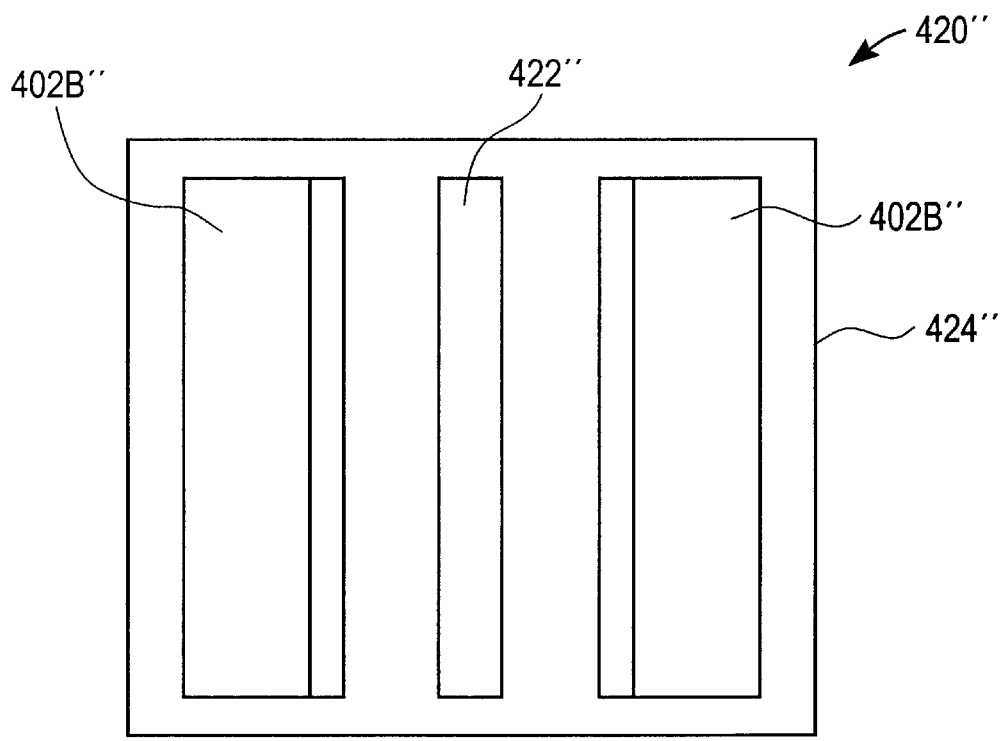

FIG. 3B is a cross-sectional schematic view of another alternative embodiment of the invention showing magnetic apparatus 372 for providing a stabilizing and a repulsive magnetic field according to the present invention. FIGS. 3C and 3D illustrate in plan view alternative embodiments corresponding to the cross-section shown in FIG. 3B wherein first array 420' is an annular configuration and first array 420" is a parallel configuration. (Reference numerals with (') and (") correspond to the same numbers in the description below.)

Magnetic apparatus 372 is provided with the configuration similar to that of apparatus 370 of FIG. 3A, except that first magnetic array 420 includes an additional third magnet 422 disposed between magnets 402A, 402B, secured to housing 424, and sealingly enclosed by the cover 426. Third magnet 422 may be generally smaller and have less magnetic intensity than the other two magnets 402A, 402B. Magnet 422 is also oriented to have its south pole on its upper face opposite to the surrounding magnets. Magnetic flux lines, 421A, 421B emanating from the magnets 402A, 402B are attracted by the south pole of third magnet 422 and directed thereto by a steeper slope or differential descending into the valley region 423. Because of a smaller repulsive force in valley 423, peak 511 of second magnetic array 500 can approach magnetic array 420 or penetrate further into the magnetic field of first magnetic array 420 in its theoretical equilibrium state. This embodiment allows an overlap to a greater extent between peak 511 of second magnetic array 500 with peaks 421A, 421B of first magnetic array 420. Accordingly, any radial movement of the second magnetic array 500 along the x-direction is opposed by stronger radial force component. Therefore, this arrangement may significantly enhance the radial stability as well as the self-aligning capability of the magnetic apparatus 372.

Figure 3E:
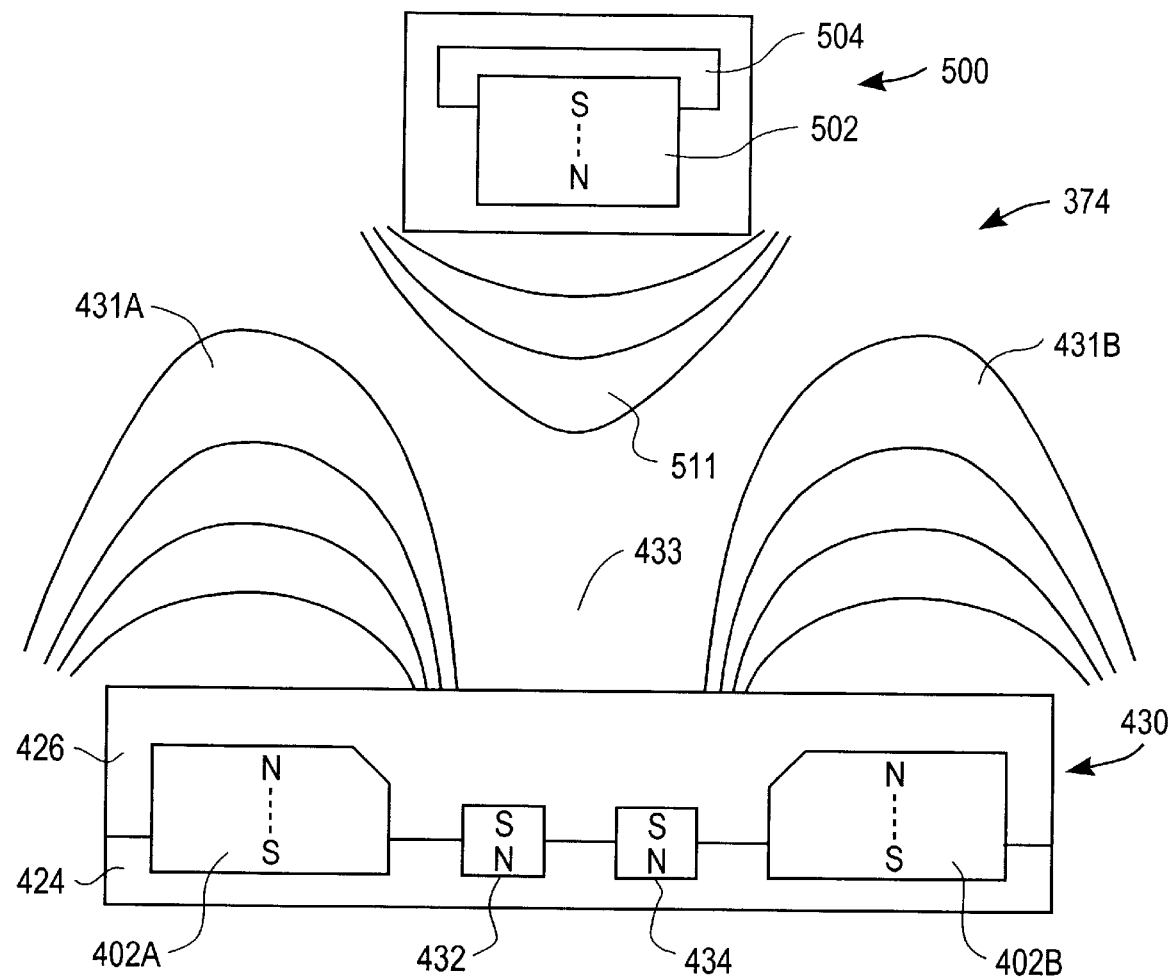
FIG. 3E is a cross-sectional schematic view of a magnetic apparatus for constraining magnetic field according to a further alternative embodiment of the present invention.

FIG. 3E is a cross-sectional schematic view of further alternative magnetic apparatus for constraining motion according to the present invention. Magnetic apparatus 374 has the configuration substantially similar to that of FIG. 3B, except that main magnets 402A, 402B of first magnetic array 430 are separated by a larger distance, and that a third and a fourth magnet 432, 434 are disposed therebetween. Both third and fourth magnets 432, 434 are arranged to have the south poles on their upper faces, facing the opposing array. Accordingly, magnetic flux lines emanating from magnets 402A, 402B are attracted by the south poles of third and fourth magnets 432, 434, increasing the slope of the equipotential lines descending into valley region 433. Compared to valley 423 of FIG. 3B, third and fourth magnets 432, 434 create a deeper and wider valley 433, with weak magnetic intensity. Because of smaller repulsive forces in wider valley 433, peak 511 of the second magnetic array 500 can penetrate the magnetic field of array 430 to a greater degree, but also limit displacement radially from its equilibrium state since it is substantially opposed by neighboring field peaks 431A, 431B of the first magnetic array 430. As will be appreciated by the persons skilled in the art, the precise characteristics and interaction of the magnetic arrays may be controlled by altering the characteristics, in particular the strength of the inner and outer magnets in array 430. For example, the strength or intensity of opposite polarity center magnets 432 and 434 may be increased to provide an attractive force which counterbalances the repulsive force of the outer magnets, thereby providing an apparatus which enhances or increases the stability in a joint rather than only reducing the joint reactive forces. It is appreciated that center magnets 432, 434 may have the same direction of polarity as peripheral magnets 402A, 402B.

Figure 3F:
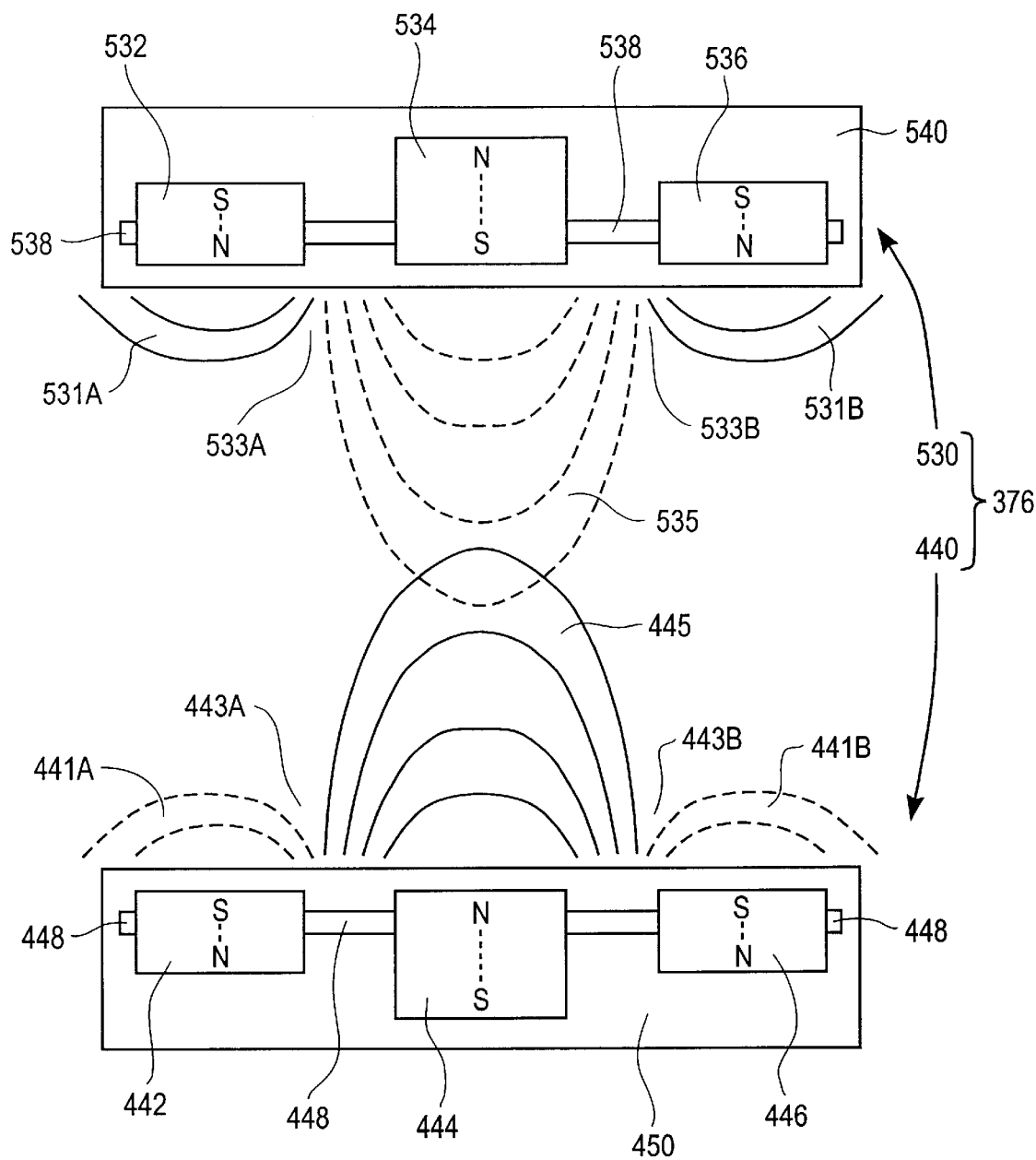
FIG. 3F is a cross-sectional schematic view of another magnetic apparatus for constraining magnetic field according to another alternative embodiment of the present invention.

FIG. 3F is a cross-sectional schematic view of another alternative embodiment of a magnetic apparatus 376 according to the present invention. In this embodiment, first magnetic array 440 includes three magnets 442, 444, 446. Center magnet 444 has its north pole on its upper face and two peripheral magnets 442, 446 have their south poles on the upper face. After being secured to frame 448, all three magnets 442, 444, 446 are further embedded in an outer housing 450 made of implantable material. In general, the center magnet 444 is designed with larger magnetic strength than the peripheral magnets 442, 446. Because the opposite poles are disposed on the same side, the composite magnetic field of the first magnetic array 440 includes two peaks 441A, 441B of the equipotential lines of magnetic fluxes emanating from the south poles of the peripheral magnets 442, 446, and a peak 445 of the equipotential lines of magnetic fluxes with opposite polarity and emanating from the north pole of the center magnet 444. Between peaks 441A, 445, and 441B are also formed two valleys 443A, 443B.

The second magnetic array 530 also includes three magnets 532, 534, 536. Center magnet 534 has its south pole on its upper face and two peripheral magnets 532, 536 have their north poles thereon. All three magnets are also secured to frame 538, arranged to have their upper faces flush with each other, and embedded in an outer housing 540 made of implantable material. Center magnet 534 is also designed to have greater magnetic strength than peripheral magnets 532, 536. Similar to that of first magnetic array 440, the composite magnetic field of second magnetic array 530 includes two peaks 531A, 531B of the equipotential lines originating from the north poles of peripheral magnets 532, 536, and peak 535 of the equipotential lines with the opposite polarity originating from the south pole of center magnet 534. Two valleys 533A, 533B are also formed between peaks 531A, 535 and 531B. The composite magnetic fields of first and second magnetic arrays 440, 530 form two adjacent and interacting magnetic fields. Since the poles of magnets 532, 534, 536 of second magnetic array 530 face the poles of magnets 442, 444, 446 of first magnetic array 430 having opposite polarity, the two arrays are attracted together. The composite fields further interact as a result of the alternative polarity to be drawn together in a specific orientation and to resist rotation with respect to each other.

The embodiment of FIG. 3F provides 1-, 2- or 3-dimensional structural stability to the magnetic apparatus 376. For example, when a static or dynamic load is exerted on the second magnetic array 530, the attractive force of magnetic apparatus 376 prevents displacement of second magnetic array 530 away from the first magnetic array 440. When the magnitude of the external load surpasses a theoretical threshold, second magnetic array 530 may be uncoupled or displaced, generating a gap between magnetic arrays 440, 530. During this displacement, the mechanical energy applied to the magnetic apparatus 376 is converted to the potential energy of the interacting magnetic field in the form of distorted or stretched equipotential lines. When the radial load is removed or decreased, the potential energy of the interacting magnetic field is converted back to the mechanical energy, thereby pushing second magnetic array 530 toward first magnetic array 440, preferably by aligning its center line (axis) with that of first magnetic array 440. As will be discussed in greater detail below, magnetic apparatus 376 thus offers structural stability particularly beneficial in applications such as fracture reduction and treatment for coupling the adjacent bone portions and maintaining the predetermined desired relationship as well as in constraining their 1-, 2-, and/or 3-dimensional motion.

In addition, the embodiment of FIG. 3F provides rotational stability by resisting rotation of the one magnetic array with respect to the other and by providing two or more parallel magnetic forces. When second magnetic array 530 is twisted, the attractive force of the magnetic apparatus 376 prevents rotation of the second magnetic array 530 about the first magnetic array 440. When the magnitude of the external load surpasses the threshold, second magnetic array 530 may be rotated, causing opposite poles of the opposing array 530 to interact and repel each other. During rotation, the mechanical energy applied to the magnetic apparatus 376 is converted to the potential energy of the interacting magnetic fields in the form of distorted or stretched equipotential lines. If the external load further increases in its magnitude, the second magnetic array 530 is further rotated and the distance between the like poles of first and second magnetic arrays 440, 530 generate the repulsive force opposing the rotation or translation. When the load is decreased or removed, the potential energy of the interacting magnetic field is converted back to the mechanical energy, allowing second magnetic array 530 to revert back to its equilibrium positioned with first magnetic array 440. As will also be discussed in greater detail below, magnetic apparatus 376 is particularly beneficial in coupling the adjacent bone portions and in preventing their 1-, 2-, and/or 3-dimensional rotation, as is often required in fracture reduction and stabilization.

The magnetic apparatus, magnetic arrays, and magnets therefor described herein above are designed and manufactured based on variety of factors, such as the anatomical part that needs to be treated, the pathologic or etiologic origins thereof, the physiological characteristics of patients, and/or the decisions made by medical experts. Once the orthopedic surgeon decides the primary purpose of orthopedic treatment, e.g., providing one or more of axial, radial, structural, and/or rotational stability, he or she may choose from a group of pre-manufactured implants according to the invention to provide appropriate characteristics that generate the contour and distribution pattern of equipotential lines and provide preferred ranges of attractive and/or repulsive force(s) associated therewith.

Various factors may effect the topographic contour and/or distribution pattern of the equipotential lines, configuration and/or location of the peaks and the valley of the equipotential lines, and the dynamic properties thereof (e.g., the packing state). Examples of such factors may include, but are not limited to, material, shape, size, polarity, strength, orientation, and distribution pattern of the magnets. Further examples may include orientation of the magnetic axis, number and/or distribution pattern of the poles on each side of the magnetic arrays, presence of insulating material around or between the magnets, and presence of symmetric, axial-symmetric or non-symmetric distribution of the magnets in the magnetic arrays (or a plurality of magnetic arrays themselves). For example, the magnetic array may include cylindrical, rectangular, annular, conical, spherical, slab-like, bar-shaped, U-shaped, and/or C-shaped magnets, and/or magnets with other geometric shapes and/or sizes suitable for the specific treatment. Magnetic intensity of a particular magnet may be altered resulting in the equipotential lines being shifted or skewed. Similar results may be obtained by changing relative positions of the magnets. In addition, by changing the configuration and orientation of one magnet with respect to the others, the equipotential lines may be altered and distribution thereof skewed in any desirable direction. For example, instead of the bell-shaped contours described in FIGS. 1C, 1E, 1F, and 1H, the equipotential lines may be arranged to have an inverse U-shaped distribution pattern. Preferably these contours will be three dimensional, such as paraboloid or rotated sinusoid as previously described in order to permit one three dimensional field to penetrate and be constrained by the other.

The composite magnetic field of a magnetic array may be quantitatively assessed utilizing the governing equations (e.g., differential equations of divergence and curl of a magnetic flux density vector) of magnetostatics or magnetodynamics, with appropriate boundary conditions and delineated properties of the conducting medium. The composite magnetic field of a complicated magnetic array may also be analytically estimated by approximating the terms of the governing equations and/or the boundary conditions. Alternatively, such solutions and/or estimations may also be obtained by numerical methods such as finite element, finite difference or boundary element analysis or by computer simulation using software which is commercially available, for example, LORENTZ from Integrated Engineering Software, Winnipeg, Manitoba, CANADA. Accordingly, specific contour- or pattern-determining factors described herein above can be optimized by a computer modeling and analysis and then selected to provide the desired function by one skilled in the art.

Conversely, the configuration of the magnets, the magnetic arrays, and/or the magnetic apparatus may be deduced from the predetermined distribution pattern of magnetic flux lines and/or equipotential lines of composite magnetic fields. In theory, the preferred configuration of the magnets and magnetic array can be obtained by finding the solution of the governing equations of magnetostatics or magnetodynamics with the desired predetermined composite magnetic fields as the boundary conditions. Solutions to such equations can be very complex. It is preferred that at least a portion of the solution be known in advance, and the analytical, numerical, and/or computer simulation method resorted to for obtaining specific details of the solutions for the governing equations. For example, in treating various joint disorders, the surgeon may decide to provide the axial and radial stability to the adjacent bone portions by using two magnetic arrays, each including two concentric magnets with the north poles in opposition. The surgeon may also determine the dimensions of the magnetic array based on the shape and size of the adjacent joint bone portions into which the magnetic arrays are to be implanted. By incorporating the detailed information into the boundary conditions and/or by assuming the basic functional characteristics of the solution (e.g., exponential, hyperbolic or polynomial terms), the analytical, numerical, and/or computer simulation may yield a more practical solution.

Alternatively, various sets of standardized orthopedic magnetic apparatus may be provided so that the surgeon may select from a set of apparatus that provides options that are suitable to the particular purpose of the orthopedic treatment. For example, depending on whether the principal purpose of orthopedic treatment is to provide axial, radial, structural, and/or rotational stability and whether the dominant driving force is the repulsive or attractive force, the surgeon may select the magnetic arrays including the magnets with desirable shapes, sizes, configuration, and/or magnetic intensity. The standardized sets may further be provided based on other criteria such as dimensions or space available for implanting the orthopedic magnetic arrays and/or the methods of coupling and securing the magnetic arrays to the adjacent bone portions.

In yet another alternative, universal orthopedic magnetic apparatus may be provided to allow the surgeon to customize the orthopedic magnetic apparatus based on the particular purpose of the orthopedic treatment. For example, a manufacturer may provide the surgeon an inventory of standardized magnets having various shapes, sizes, and/or intensities, and another inventory list of housings with universal receptacles. The surgeon or the appropriate representative may select magnets which best suit the purpose of the orthopedic treatment and position the magnets on the universal housing, thereby creating a customized magnetic array. After the magnets are sealingly enclosed by a universal enclosure, embedded or incased in an outer housing, the magnetic array thus prepared will be ready for implantation.

EXAMPLE

Figures 4A, 4E:
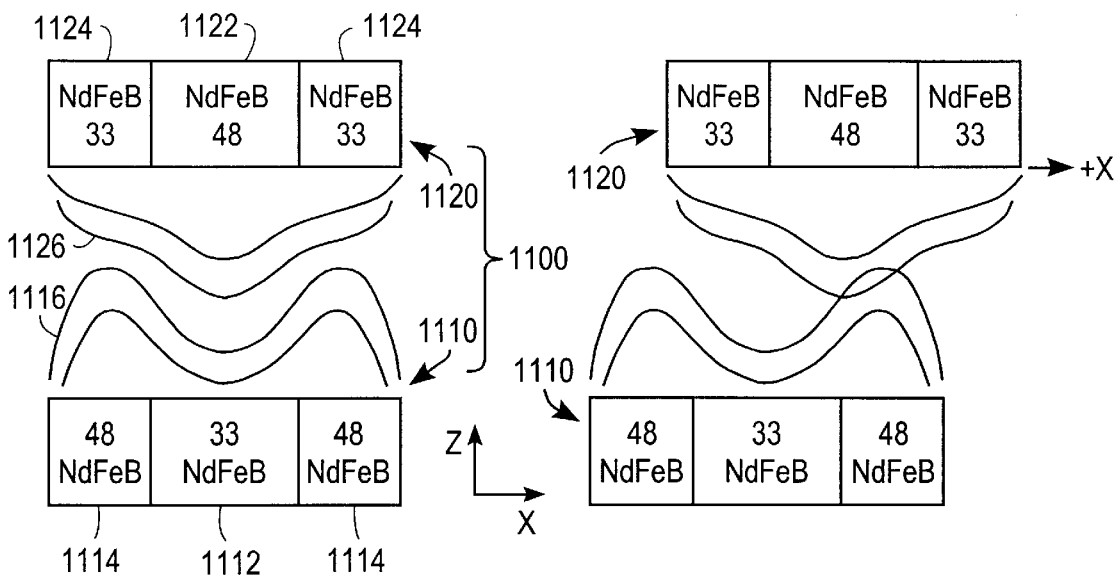
FIG. 4A is a schematic representation illustrating the interaction between two magnetic arrays as described in the Example.
FIG. 4E is a schematic representation further illustrating the interaction between the magnetic arrays shown in FIG. 4A.

The following example represents the results of a computer model of a basic array design incorporating the fundamentals of the present invention. A computer simulation was performed to determine the magnitude of the repulsive vertical and radial force components of a representative magnetic arrays. As illustrated in FIG. 4A, apparatus 1100 includes first magnetic array 1110 and a second magnetic array 1120, where both arrays include the cylindrical center magnets 1112, 1122 positioned inside annular magnets 1114, 1124. The center magnets for each array were chosen to be one inch in diameter. The annular magnets were chosen to have an O.D. of two inches and an I.D. of one inch. Each array was one inch thick. In second array 1120, central magnet 1122 was made of NdFeB 48 and outer annular magnet 1124 was made of NdFeB 33. First array 1110 had the same configuration except that the magnet materials were reversed such that the stronger NdFeB 48 was at the outside. Both the first and second magnetic arrays were oriented such that the same poles (e.g., north poles) were disposed facing each other. Therefore, first magnetic array 1110 generated the first composite magnetic field having approximately "M"-shaped (or cup shape in three dimensions) equipotential lines 1116, while the second magnetic array 1120 created the second composite magnetic field having approximately "V"-shaped (or paraboloid shape in three dimensions) equipotential lines 1126. As a result, first and second magnetic arrays 1110, 1120 tended to be forced apart from each other by the repulsive force generated therebetween.

Figure 4F:
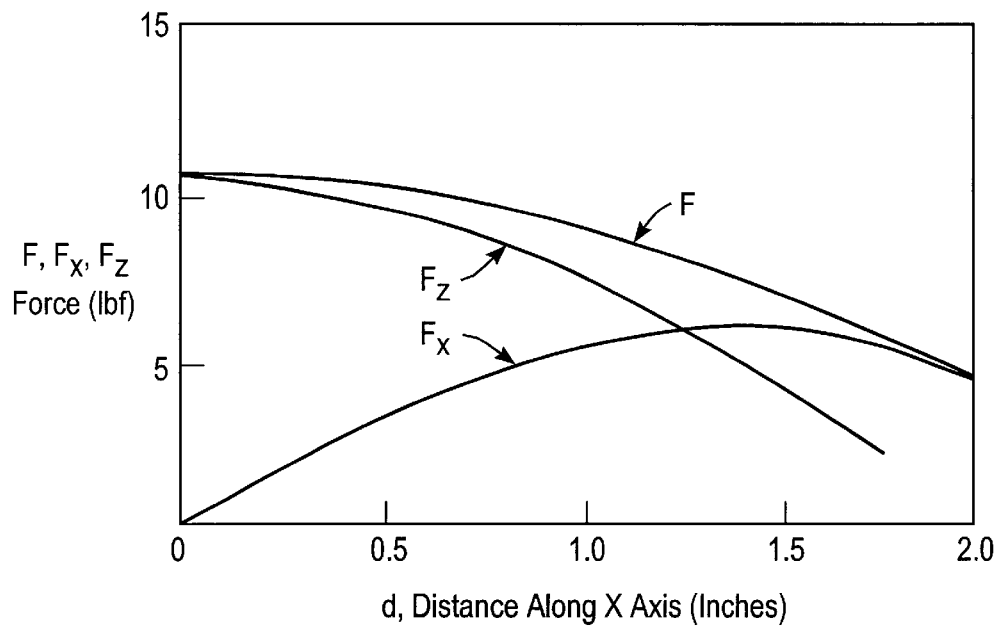
FIG. 4F is a plot of forces resulting from the interaction of magnetic arrays as explained in the Example.
Figure 4B:
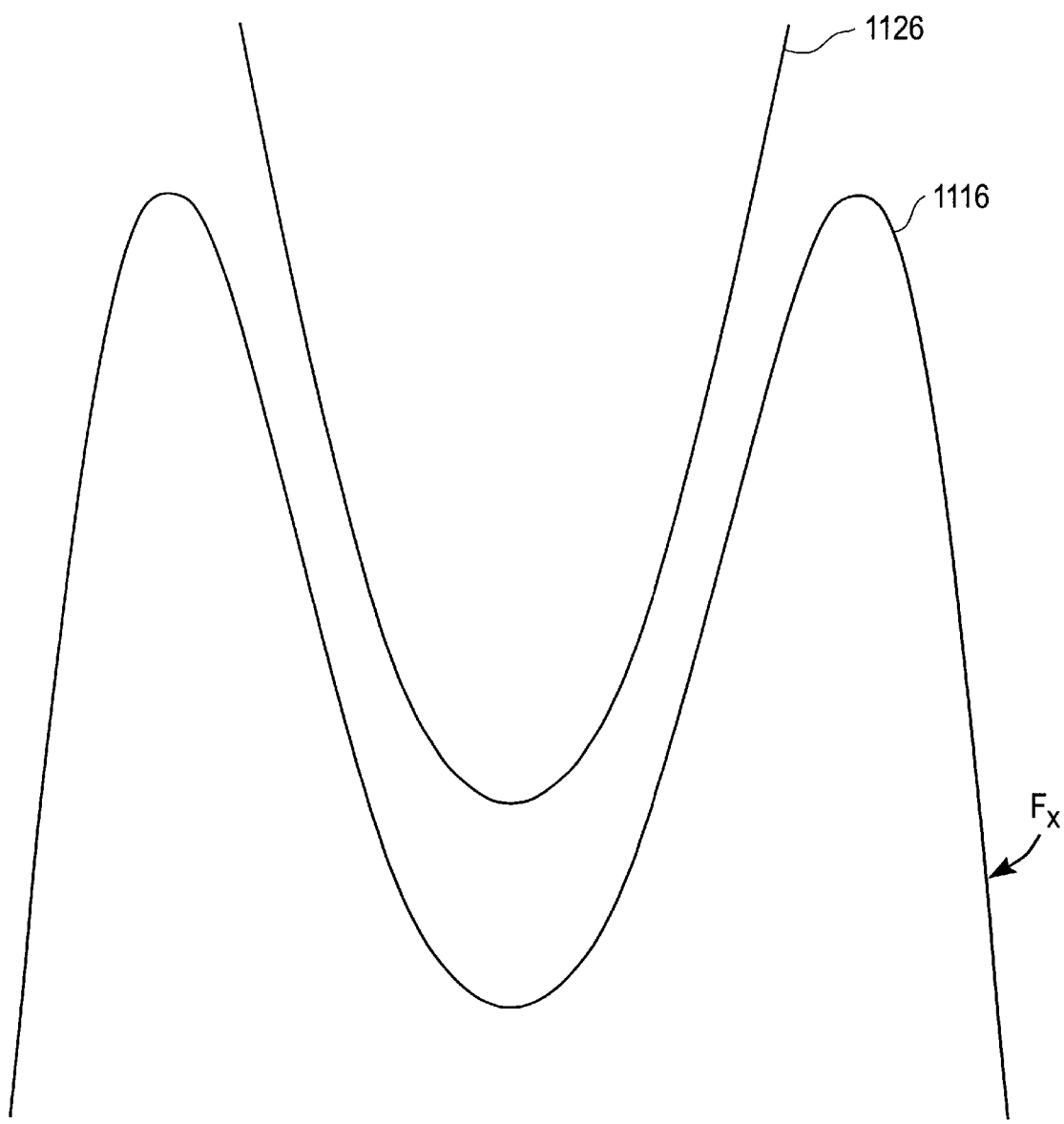
FIG. 4B is a graphical representation of the cooperating magnetic fields generated by the magnetic arrays shown in FIG. 4A.
Figure 4C:
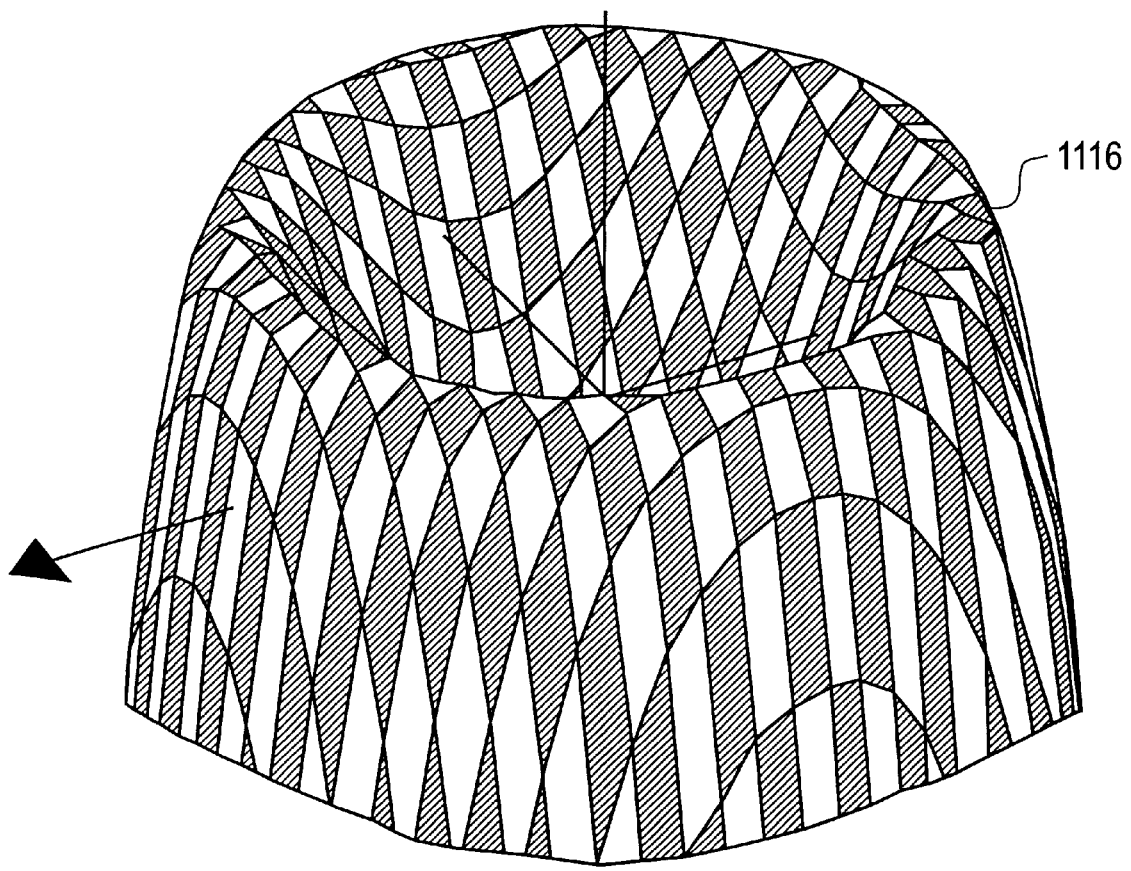
FIG. 4C is a graphical representation in three dimensions of the magnetic field generated by the lower magnetic array in FIG. 4A.
Figure 4D:
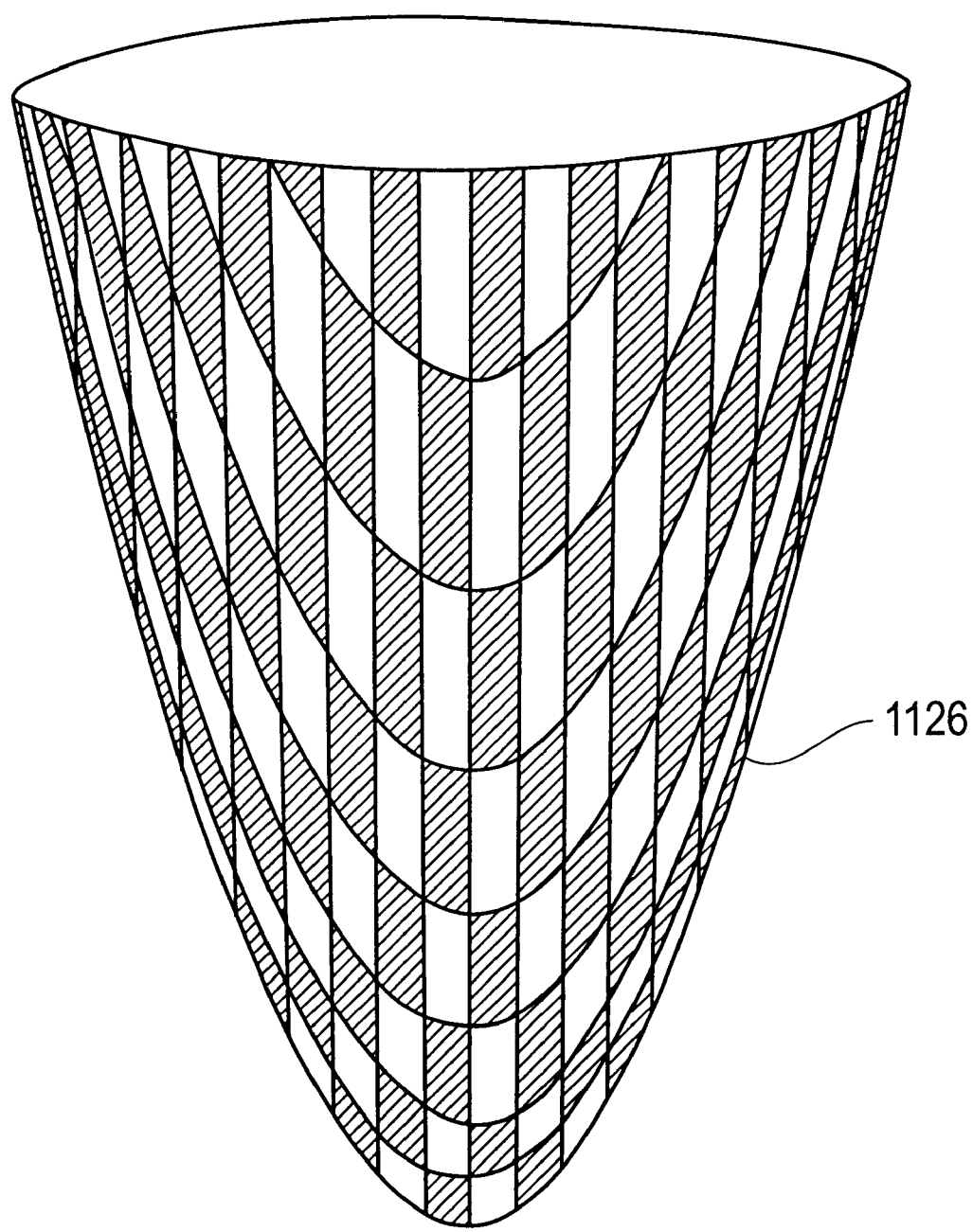
FIG. 4D is a graphical representation in three dimensions of the magnetic fields generated by the upper magnetic array in FIG. 4A.

The magnetic fields generated by the arrays are represented graphically in FIGS. 4B, 4C and 4D. For magnetic array 1120, a cross-section of the magnetic field and equipotential lines 1126 is approximated by the formula, $y=3x^2$ and for magnetic array 1110, a cross-section of the magnetic field and equipotential lines 1116 is approximated by the formula, $y=3 \sin(x^2)$. In FIG. 4B, the interacting magnetic fields are represented as positioned approximately 0.75" apart in the vertical direction to illustrate how upper magnetic array 1120 and its magnetic field 1126 may be retained by the cup shaped magnetic field 1116 of lower magnetic array 1110. (This spacing is illustrative only and may not represent actual spacing.) FIG. 4C illustrates a perspective view of the magnetic field 1116 generated by lower magnetic array 1110 in three dimensions, obtained by the formula, $z—3 \sin(x^2+y^2)$. Similarly, FIG. 4D illustrates a perspective view of the magnetic field 1126 generated by upper magnetic array 1120 in the three dimensions, obtained by the formula, $z=3(x^2+y^2)$.

To illustrate the interaction between the cooperating magnetic fields of the two arrays, second magnetic array 1120 was positioned approximately one inch above first magnetic array 1110. Second magnetic array 1120 was then moved in the positive x-direction while maintaining the same vertical distance therebetween as depicted in FIG. 4E. Commercial software was used to simulate the variations in magnitude of the net repulsive force and its radial and axial components as the relationships between the two magnetic arrays of the apparatus were changed.

FIG. 4F is a plot of the axial and radial repulsive force components generated from the sample magnetic apparatus as the upper array was moved radially. Symbols "F," "$F_X$," and "$F_Z$," represent the magnitude of the total net repulsive force, the magnitude of the force component in the radial direction (x-direction), and the magnitude of the force component in the vertical direction (z-direction), respectively, where the net force, F, is calculated as a square root of a sum of squares of $F_X$ and $F_Z$. The radial offset distance between the central axes of magnetic arrays 1110, 1120 is denoted by a symbol "d" along the abscissa. ($F_Y$ was set according to the conditions of the model to be ~0).

As shown in FIG. 4F, magnetic arrays 1110, 1120 do not exert radial force when their center lines are aligned in the x-z plane (i.e., where d=0). As the second magnetic array is displaced from the aligned equilibrium position in the x-z plane, the lateral force component ($F_X$) increases while the net vertical force component ($F_Z$) decreases. When d is approximately +/−1.2 in., the radial force component ($F_X$) equals the vertical force component ($F_Z$) and surpasses it thereafter. When (d) is 2.0 in., more than 95% of the net repulsive (F) are attributed to the radial force component ($F_X$).

This simulation demonstrates the interaction between cooperating magnetic fields of magnetic arrays according to the invention. In particular, in this example the self-centering and retention features of properly designed arrays are demonstrated.

Figure 5A:
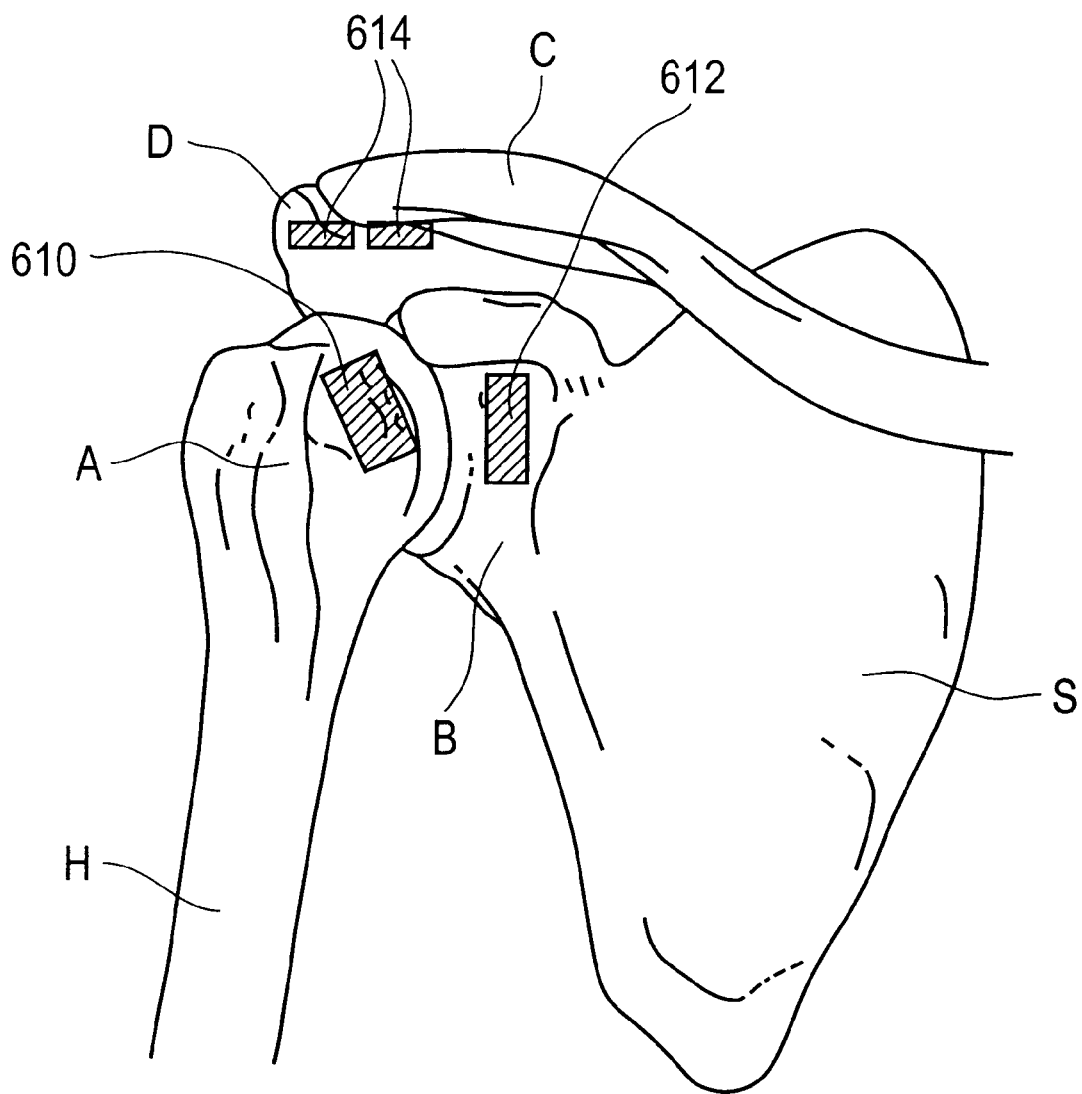
FIGS. 5A and 5B are diagrammatic representations of alternative embodiments of the present invention directed to joint treatment or stabilization.
Figure 5B:
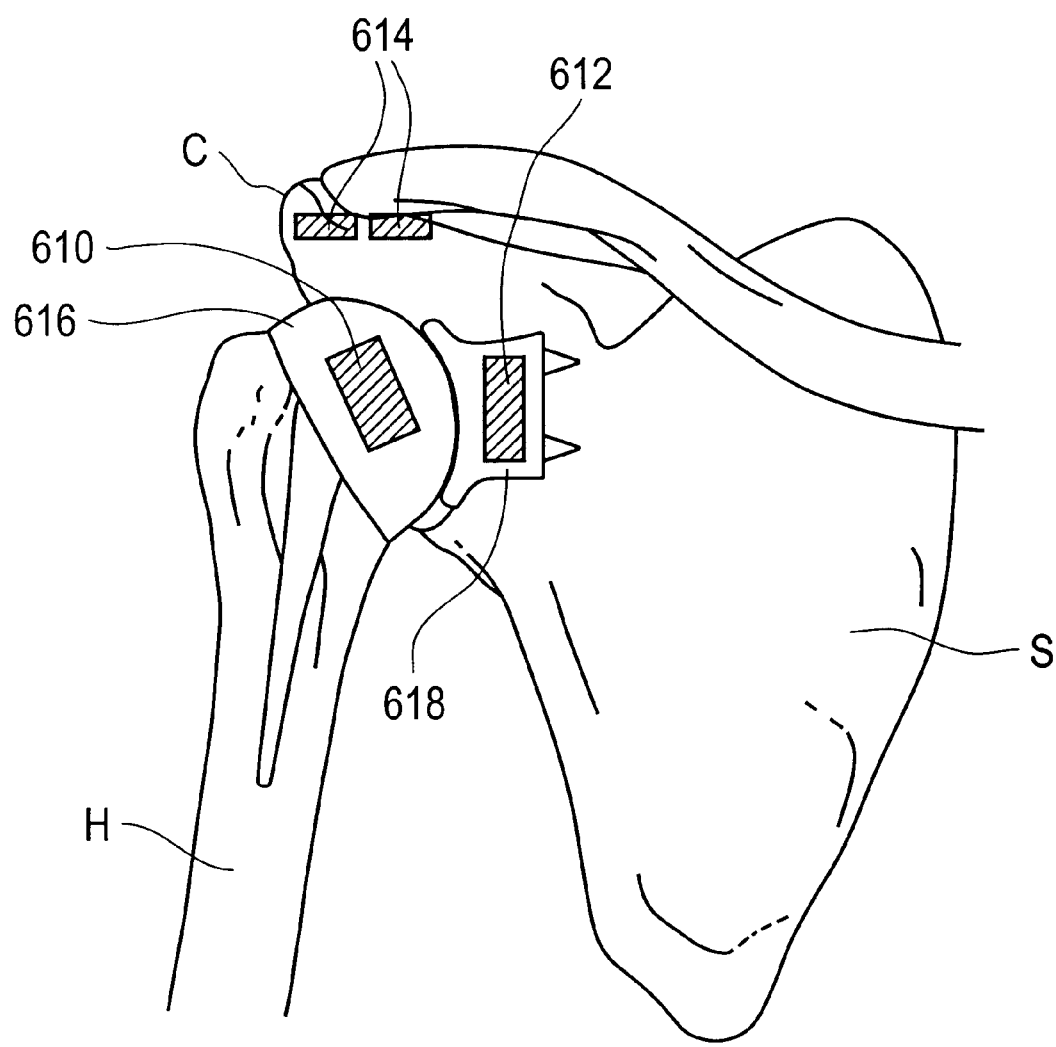

By way of further example, FIGS. 5A and 5B illustrate alternative embodiments for treatment of shoulder conditions utilizing magnetic array implants according to the present invention. As depicted in FIG. 5A, the shoulder joint includes the humerus (H), scapula (S) and the clavicle (C). Matched magnetic arrays 610, 612, and 614 according to the present invention are placed in the humeral head (A), the glenoid (B), and the acromion (D), respectively. The magnetic arrays may be designed to provide a significant repulsive force between the adjacent bone portions to reduce or prevent contact and wear of the joint components. Less significant attractive forces between the magnets may be used to stabilize the bones of the shoulder joint in an anatomical or near-anatomical configuration. The attractive forces of the matched magnetic arrays will tend to compensate for any forces that are disruptive to the normal configuration of the bones in the shoulder joint. Centralizing forces stabilize the bones of the shoulder joint by keeping them aligned in their functionally anatomical position. For example, magnetic arrays 610 and 612 may comprise a pair of arrays having a similar design to that of magnetic arrays 1110 and 1120 as described in the Example above. The shape of the magnetic field created by array 610 would cooperate with the shape of the magnetic field generated by array 612 such that interaction between the magnetic fields would provide the necessary centralizing forces. To the extent attractive forces are used in a particular implementation, such attractive forces may be created and controlled as described in connection with the alternative embodiments shown in FIGS. 3B and 3E, above. This embodiment also illustrates that not all magnets in an array need act in the same plane. In particular, magnetic array 610 includes magnets acting upward to cooperate with array 614 positioned in the acromion and further includes magnets acting generally laterally to cooperate with array 612 positioned in the glenoid.

FIG. 5B illustrates a further alternative embodiment wherein magnetic arrays according to the present invention are utilized to augment the design of current prosthetic elements. As shown in FIG. 5B, magnetic array 610 is positioned within humeral head replacement prosthesis 616. Likewise, magnetic array 612 is positioned within glenoid replacement prosthesis 618. The cooperation and effect of the magnetic arrays are as described above. Prostheses 616, 618 may be implanted according to known techniques. Utilizing magnetic arrays according to the present invention with known prostheses may prevent or decrease wear and increase stability, thereby prolonging prosthesis life.

Figure 6:
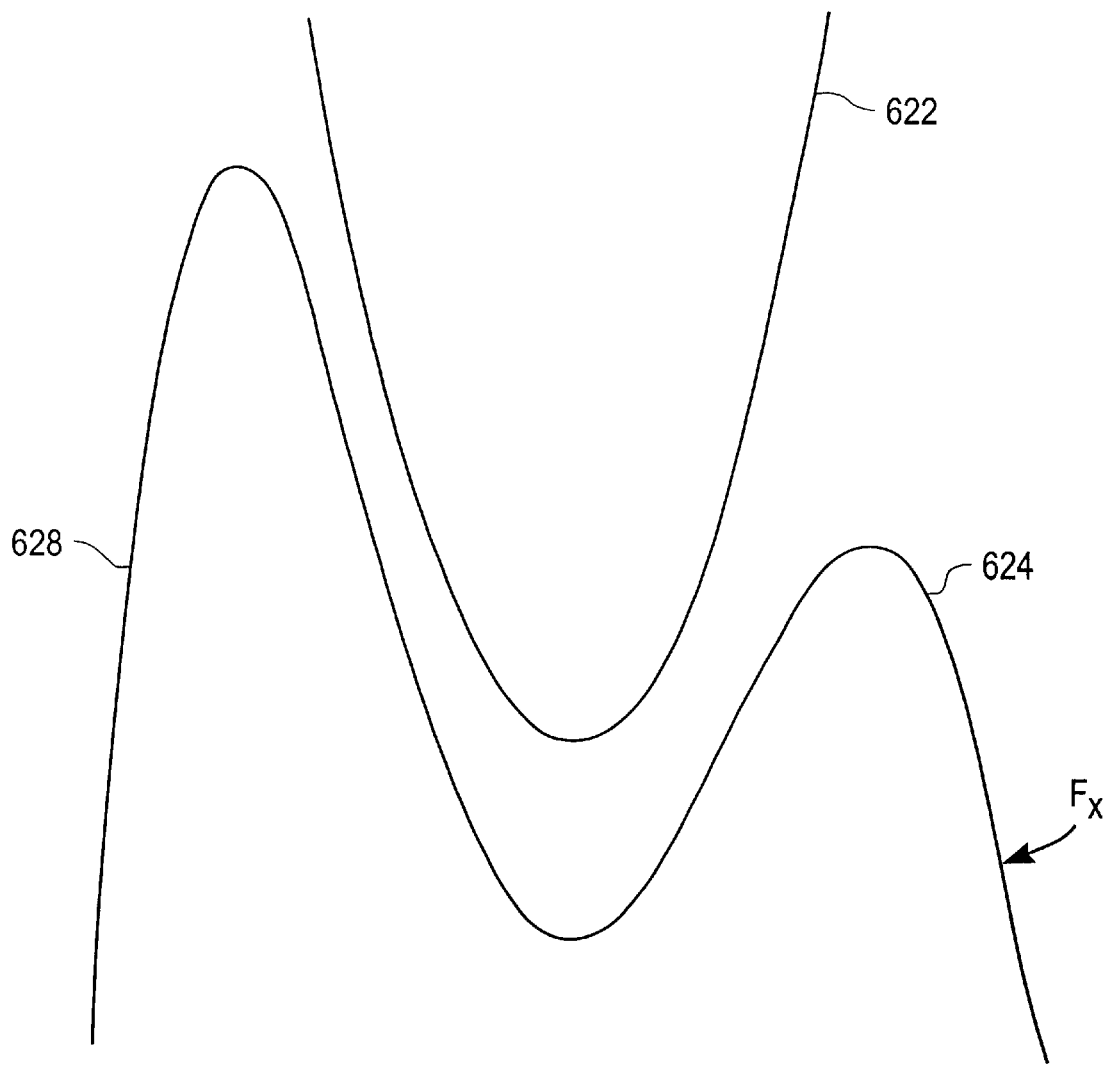
FIG. 6 is a graphical representation of cooperating magnetic fields in an alternative embodiment of the invention.

As previously mentioned, asymmetric arrays may be utilized to address particular problems or situations faced by surgeon. For example, in order to increase anterior stability in a shoulder joint application, a surgeon may select magnetic arrays having cooperating fields 622 and 624 as shown in FIG. 6. In this embodiment, magnetic field 624 is formed asymmetrically to provide increased translational stability along axes orthogonal to the magnetic axis in region 628. This may be accomplished, e.g., by utilizing a magnetic array such as array 10 shown in FIG. 1A and by altering two to four of the peripheral magnets to have weaker or stronger magnetic intensity.

Figure 7:
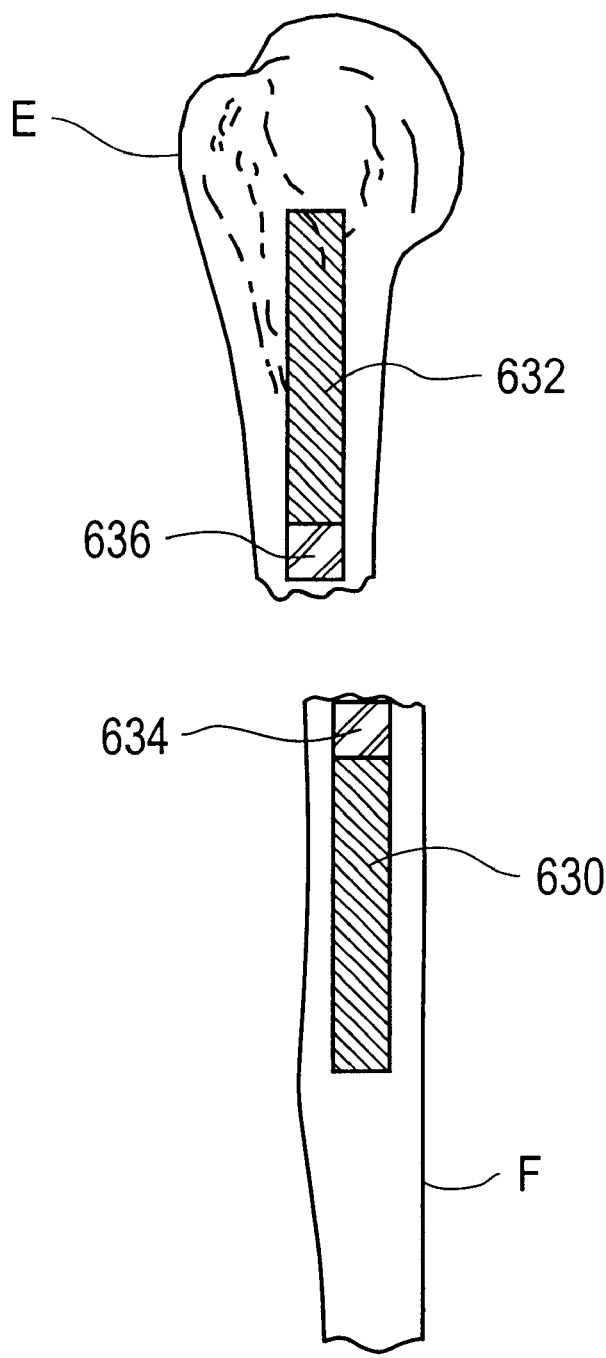
FIG. 7 is a diagrammatic representation of a further alternative embodiment of the present invention for fracture treatment and reduction.

FIG. 7 illustrates a further alternative embodiment of the present invention wherein magnetic arrays according to the invention are utilized for fracture reduction and stabilization. In this example, a long bone is fractured into two bone portions (E, F). A fracture reducing implant is provided in two components formed as intramedullary rod portions 630 and 632. Disposed at one end of each rod portion are magnetic arrays 634 and 636. In such an arrangement, the attractive forces between magnetic arrays 634 and 636 align and stabilize the bone portions resulting from the fracture. The paired magnetic arrays may also allow micro-motion between the fragments and set up a magnetic field in the environs of the fracture, which may be favorable to promoting fracture healing. An example of a preferred arrangement of arrays for this application would be such as that shown in FIG. 3F, above.

Figure 8A:
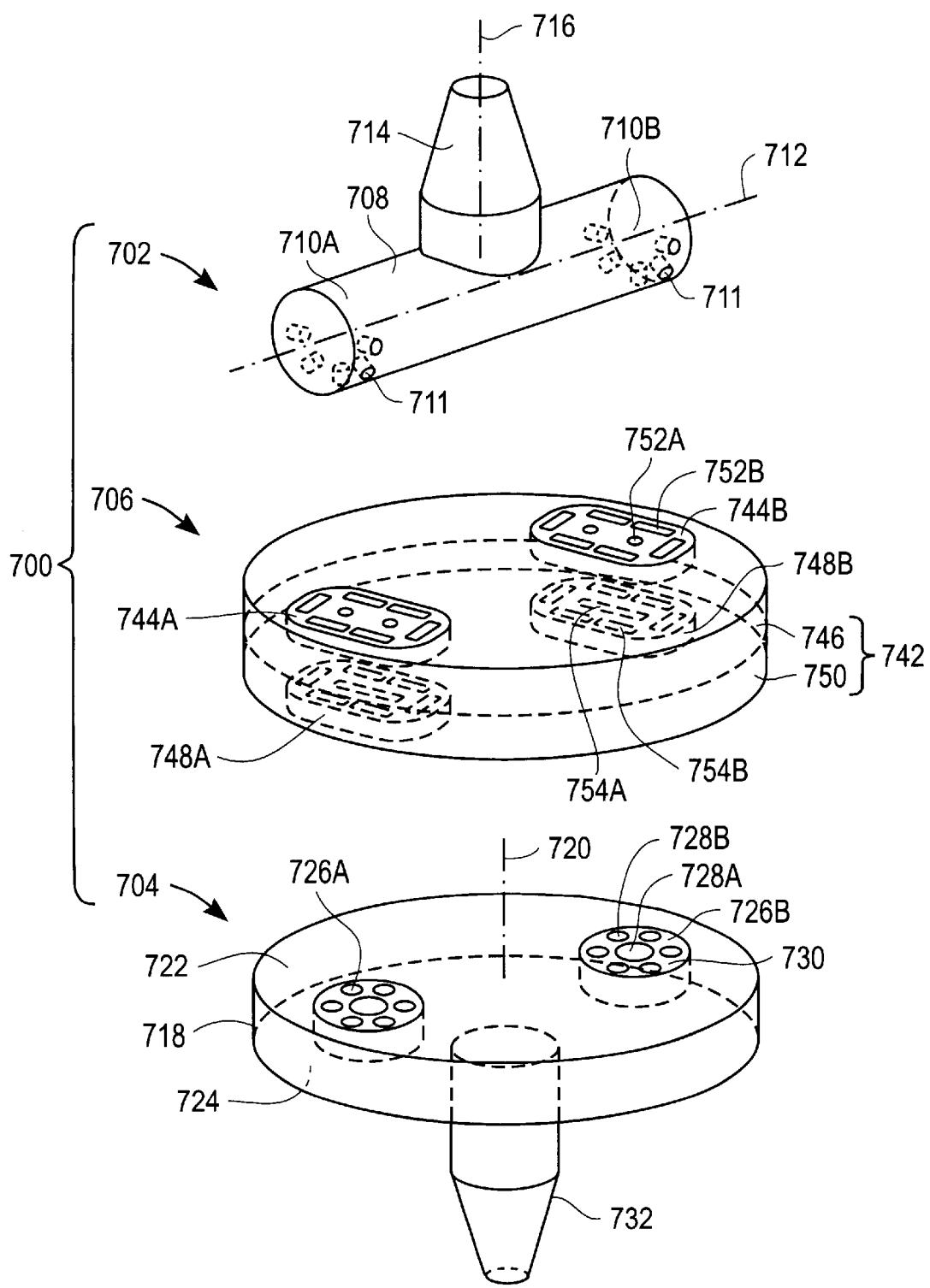
FIG. 8A is a schematic diagram of an exemplary orthopedic prosthesis with a floating component with magnetic arrays according to the present invention.

In a further alternative embodiment of the invention, a floating component, having at least one magnetic array generating mobile composite magnetic fields therearound may be disposed between two fixed components as shown, e.g., in FIG. 8A. By floating component it is meant herein that the component is movably disposed between other components, restrained substantially by the magnetic fields generated between the components or other passive means and not by direct or rigid fixation to the bone or other component. Such floating component may be incorporated into pre-implanted prosthesis components in order to augment, attenuate or modify pre-existing magnetic fields in magnetic components or to add advantages of magnetic components to traditional implants. Alternatively, the floating component and securable prosthesis components may be provided as a unit and implanted together into a joint during a single procedure. FIGS. 8–11 illustrate exemplary embodiments of orthopedic prostheses incorporating such floating components. Persons of ordinary skill in the art will appreciate that the figures are schematic representations that illustrate the principles of the invention and the configurations of implants according to the invention may vary in actual practice.

According to one embodiment, shown in FIG. 8A, orthopedic prosthesis 700 typically includes a first (prosthesis) component 702 to be secured to a first bone portion, a second (prosthesis) component 704 to be secured to a second bone portion, and a floating component 706 to be movably and/or detachably incorporated between first and second (prosthesis) components 702, 704.

In the illustrated exemplary embodiment, first component 702 has an elongated cylindrical body 708 and includes a pair of first magnetic arrays 710A, 710B secured to each end portion of body 708. The body may be of different shape. Body 708 is preferably disposed generally horizontally along a longitudinal axis 712 thereof. Each first magnetic array 710A, 710B has an array of magnets 711 spaced apart along an arcuate circumference of cylindrical body 708 at equal distance and/or equal angle about longitudinal axis 712 of body 708. As shown in the figure, magnets 711 are arranged in a lower portion of the circumference of body 708. As will be discussed in greater detail below, each first magnetic array 710A, 710B generates a composite magnetic field generally transverse or perpendicular to longitudinal axis 712 of body 708. An anchor portion 714 is attached to body 708 and is preferably shaped and sized to be securable to a receiving socket provided in the first bone portion by, e.g., static mechanical interaction or interference, cements, adhesives, and the like.

Again, in the illustrated exemplary embodiment, second component 704 has a body 718 with a longitudinal axis 720 top and bottom surfaces 722, 724. Second component 704 includes a pair of second magnetic arrays 726A, 726B on top surface 722 of body 718, each including a center magnet 728A surrounded by symmetrically arranged peripheral magnets 728B. Other array configurations may be provided. Second magnetic arrays 726A, 726B are positioned adjacent to top surface 722 of body 718 so that top surfaces 730 of second magnetic arrays 726A, 726B act at top surface 722 of body 718. As discussed above, such second magnetic arrays 726A, 726B create composite magnetic fields defined by equipotential lines having a shape dictated by the individual magnet strength and placement as described herein. Attached to bottom surface 724 of body 718 is anchor 732 securable to the second bone portion.

Floating component 706 includes body 742, preferably shaped to match the mating components and/or anatomical space, a pair of third magnetic arrays 744A, 744B secured to upper section 746 of body 742 and another pair of fourth magnetic arrays 748A, 748B secured to lower section 750 thereof. Third magnetic arrays 744A, 744B are positioned at pre-selected locations of upper section 746 such that they can interact with first magnetic arrays 710A, 710B of first component 702 and create first interacting dynamic magnetic fields therebetween (refer to magnetic fields 770 of FIGS. 8B and 8D). In an exemplary embodiment, each third magnetic array 744A, 744B may include at least two linearly arranged center magnets 752A which are encircled by symmetrically arranged peripheral magnets 752B. As discussed above, linearly arranged center magnets 752A with the peripheral magnets can generate an elongated composite magnetic field which allows limited controlled motion, stabilization, and self-centering of first component 702. Fourth magnetic arrays 748A, 748B are positioned at desirable locations of lower section 750 of body 742 so that they can interact with second magnetic arrays 726A, 726B of second component 704 and generate second interacting dynamic magnetic fields therebetween (refer to magnetic fields 780 and 796 of FIGS. 8B and 8D, respectively). Similar to magnetic arrays 726A and 726B of second component 704, each fourth magnetic array 748A, 748B has a center magnet 754A and peripheral magnets 754B disposed therearound, with an exception that center magnet 754A as shown has an elongated shape and, therefore, creates an elongated composite magnetic field therearound.

Each element of foregoing first, second, and floating components 702, 704, 706 may be made of any biocompatible and implantable materials having desirable mechanical strength and biological and/or chemical inertness. More particularly, such materials preferably have intrinsic mechanical properties enough to support static and dynamic mechanical loads generated during normal function of the joints. Examples of such materials may include, but are not limited to, metal, stainless steel, ceramics, and other composite materials. In addition, the center and peripheral magnets of foregoing magnetic arrays 710A, 710B, 726A, 726B, 744A, 744B, 748A, 748B may be made of any of the aforementioned magnetic, diamagnetic, paramagnetic, ferromagnetic, anti-ferromagnetic, and/or ferrimagnetic materials.

As discussed above, the magnets of the foregoing magnetic arrays preferably have desirable shapes, sizes, and/or magnetic strengths to generate pre-determined composite magnetic fields therearound. Such magnets may further be arranged in various configurations to effect different composite magnetic fields. Accordingly, orthopedic prosthesis 700 of the present invention can generate various interacting dynamic magnetic fields which can be characterized by, e.g., repulsive or attractive forces which in turn contribute to stabilizing the orthopedic prosthesis components, constraining movement of such components, self-centering one component with respect to the others, absorbing or dampening external forces and/or shocks exerted thereon, and the like.

Figure 8B:
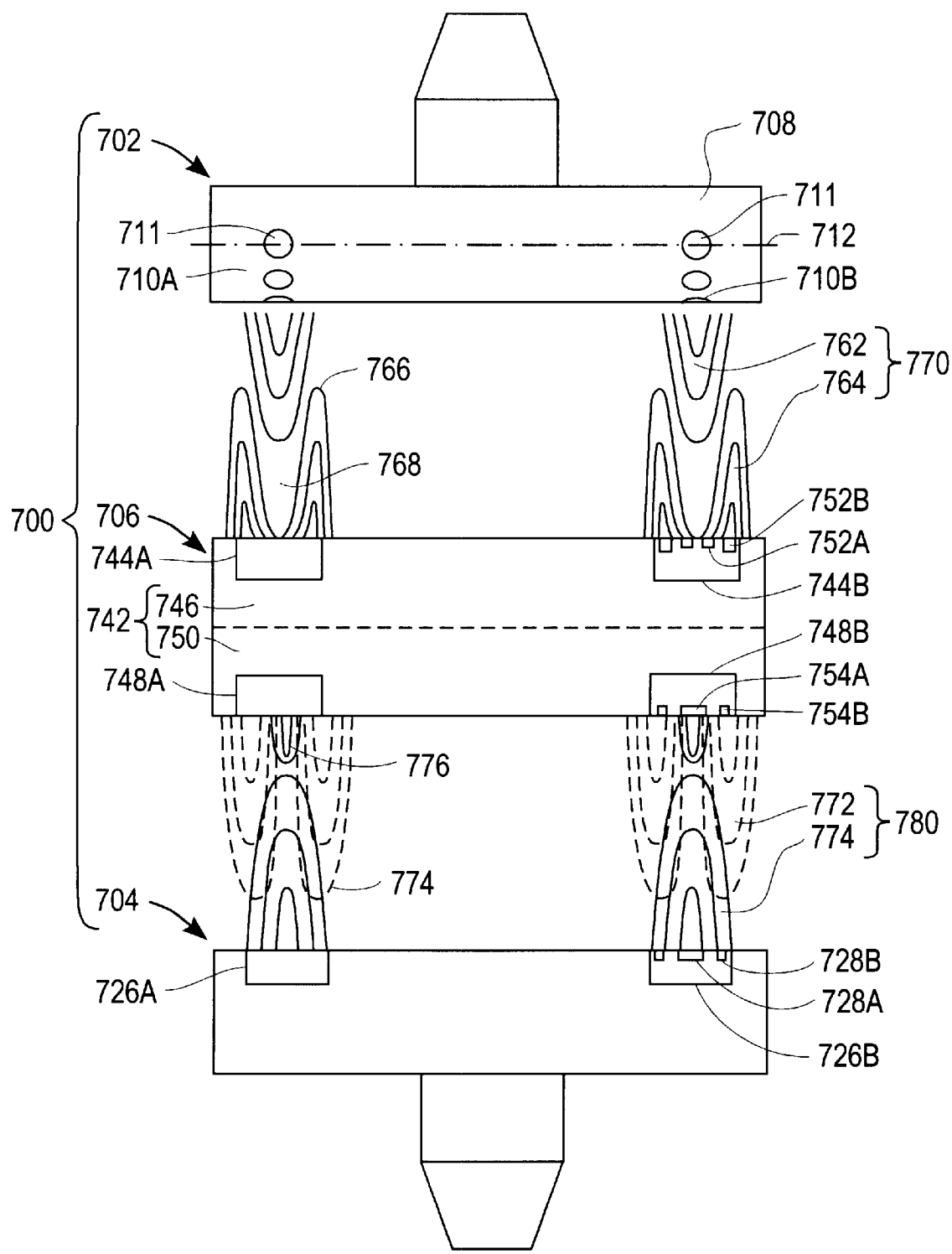
FIG. 8B is a schematic view of exemplary dynamic magnetic fields generated between the securable and floating components of the orthopedic prosthesis of FIG. 8A according to the present invention.

FIG. 8B is a schematic view of exemplary dynamic magnetic fields generated between the securable and floating components of the orthopedic prosthesis of FIG. 8A according to the present invention. Magnets 711 of first magnetic arrays 710A, 710B are arranged such that the first poles (e.g., the north poles) are exposed on the surface of body 708 of first component 702. Therefore, first magnetic arrays 710A, 710B can generate a pair of first composite magnetic fields 762 on end portions of body 708, where each composite magnetic field 762 is characterized by the equipotential lines which form an arcuate wedge or blade extending outward along the arcuate circumference of body 708. Furthermore, such equipotential lines are substantially transverse to longitudinal axis 712 of body 708, and have a profile substantially as shown. As shown in the figure, however, magnets 711 of first magnetic arrays 710A, 710B encircle only a lower half of the circumference of body 708. Thus, the foregoing wedge-like equipotential lines span out about 180° about longitudinal axis 712 of body 708. To the contrary, center magnets 752A of third magnetic arrays 744A, 744B are positioned to expose the second poles (e.g., the south poles) on top of upper section 746 of body 742 and surrounded by peripheral magnets 752B which expose the opposite (north) poles thereon. Accordingly, each third magnetic array 744A, 744B generates a third composite magnetic field 764 defined by equipotential lines forming a "trough" characterized by an elongated loop-shaped peak region 766 enclosing an elongated valley region 768 therein. Accordingly, when first and floating components 702, 706 are positioned proximate to each other, first and third composite magnetic fields 762, 764 of the same polarity define first interacting dynamic magnetic fields 770 characterized by repulsive forces pushing first and floating components 702, 706 apart from each other. It is appreciated that center magnets 752A with the second (south) polarity pull first composite magnetic field 762 further into valley region 768 of trough-shaped third composite magnetic field 764, and enhances stabilization or self-centering of first component 702 with respect to floating component 706.

First interacting dynamic magnetic fields 770 further allow two additional movements between first and floating components 702, 706. First, valley region 768 of third magnetic arrays 744A, 744B receive and allow angular displacement of the arcuate wedge-like equipotential lines of first magnetic arrays 710A, 710B therein. Therefore, first component 702 and/or first bone portion may rotate relative to floating component 706. In addition, an extended length of valley region 768 of third magnetic arrays 744A, 744B allows linear displacement of the wedge-like equipotential lines of first magnetic arrays 710A, 710B along its length, thereby allowing first component 702 or first bone portion to linearly translate along floating component 706.

Fourth magnetic arrays 748A, 748B are generally substantially similar to third magnetic arrays 744A, 744B, except they can also have opposite polarities. For example, center magnets 754A of fourth magnetic arrays 748A, 748B are arranged to expose their first (north) poles on a bottom surface of lower section 750, while peripheral magnets 754B have their second (south) poles exposed thereon. It will be appreciated that the magnets of these arrays may be selected based on the teachings set forth herein to provide arrays with various magnitudes and shapes of equipotential lines appropriate for the particular application. For example, fourth and second composite magnetic fields 772, 774 of opposite polarities may define second interacting dynamic magnetic fields 780 which are characterized by the attractive forces pulling floating and second components 706, 704 closer to each other.

The interacting dynamic magnetic fields created above and below the floating component serve to absorb or dampen external shear force or shock and/or external rotational force or shock (collectively "external forces") exerted on prosthesis components secured to the bone portions. Conventional orthopedic prostheses generally allow direct mechanical contact between their components and allow one of its components to move with respect to the other along a path defined on such components. Therefore, when the external force is exerted on the first (or second) component of a conventional orthopedic prosthesis, such force is transmitted to the second (first) component as an external force acting on the bone which supports the prosthesis and/or portions of the prosthesis itself. Repeated application of the external forces deforms or damages the interface where the bone contacts the prosthesis, and or anchoring cement. Extended application of such external force eventually causes the prosthesis components to become detached from the bone or otherwise damaged.

The floating component of the present invention reduces or prevents the foregoing adverse effects of the external force on the prosthesis components secured to the bone portions. For example, when the external force or shock displaces the first component from its equilibrium position with the underlying component, the composite magnetic field of the first component is misaligned with that of the floating component, and the mechanical energy associated with such lateral force is transformed into and stored as the magnetic potential energy of the first interacting dynamic magnetic fields created therebetween. It is appreciated that at least a portion of the mechanical energy is dissipated due to non-ideal conversion of one form of energy into another. Even when the external mechanical energy exceeds what can be stored in the misaligned first interacting dynamic magnetic fields, the floating component is displaced from its equilibrium position with the underlying, movably attached second component. This process further dissipates another portion of the external mechanical energy as the kinetic energy of the floating component. The remaining portion of the mechanical energy is then partitioned between the first and second dynamic interacting magnetic fields deviated from their equilibrium conditions. Although the misaligned second interacting dynamic magnetic fields may transmit some of the external force to the bone, such force constitutes only a part of the external force applied. Therefore, the floating component can attenuate and/or dampen the external force applied to the secured prosthesis components. When the external force ceases to be applied to the first component, the first and floating components are displaced back to their equilibrium positions by transforming the magnetic potential energy into kinetic energy thereof. The floating component of the present invention thus may serve as a mobile magnetic damper or bearing.

Figure 8C:
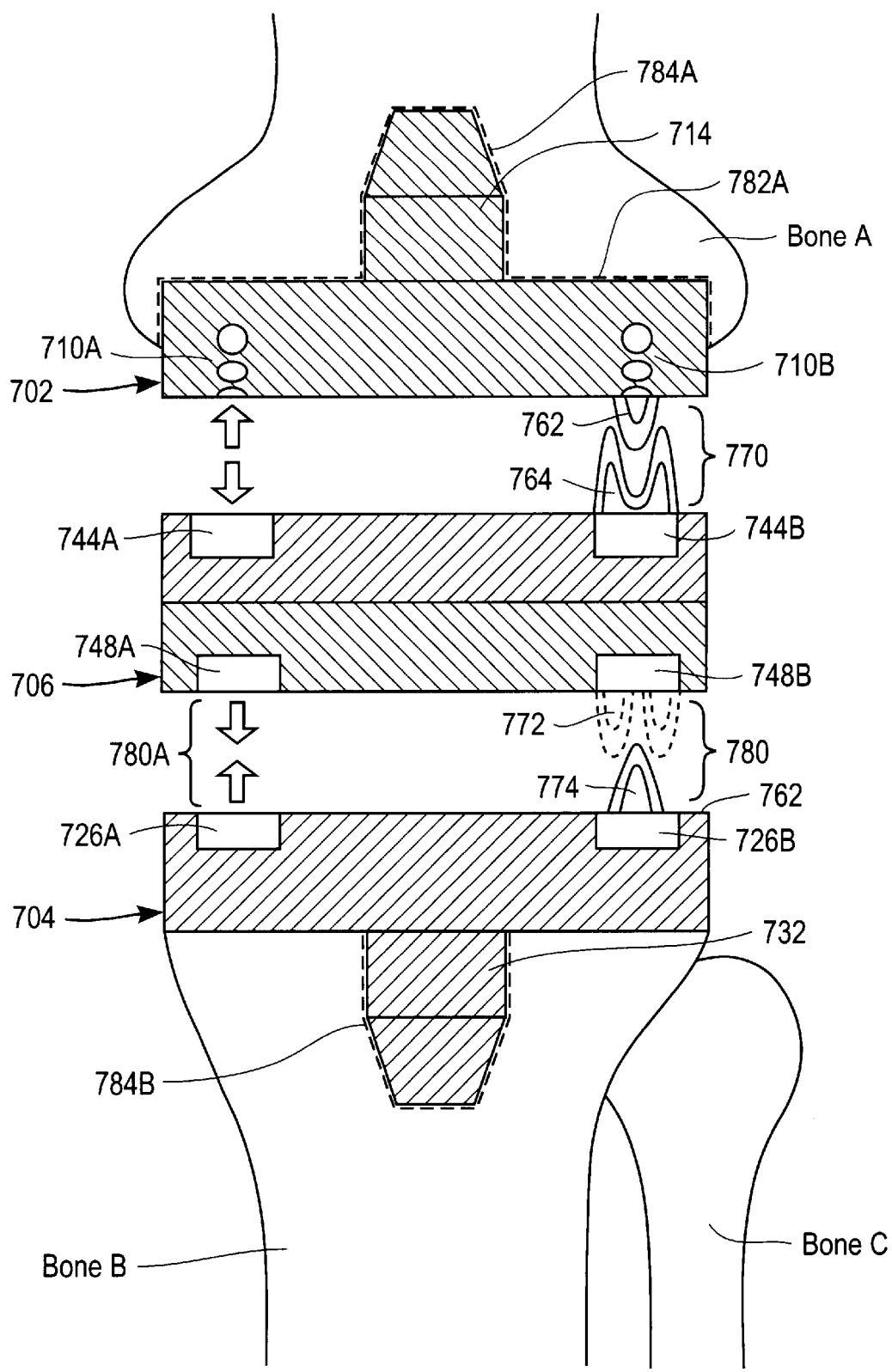
FIG. 8C is a schematic view of the orthopedic prosthesis of FIGS. 8A and 8B in operation where the prosthesis is applied to a knee joint for total knee arthroplasty according to the present invention.

FIG. 8C is a schematic view of the orthopedic prosthesis of FIGS. 8A and 8B in operation where the prosthesis is applied to a knee joint for total knee arthroplasty according to the present invention. In this procedure, first prosthesis component 702 corresponds to a femoral component, while second prosthesis component 704 thereof is a tibial component. In the figure for the total knee arthroplasty, bone A represents the femur, bone B corresponds to the tibia, and bone C is the fibula.

Tapered anchor 732 of tibial component 704 is inserted into a receiving hole 784B of bone B and affixed thereto by, e.g., static mechanical interaction, interference fit, cements, and/or adhesives. Tibial component 704 is preferably oriented so as to align major axes of composite magnetic fields 774 generated by second magnetic arrays 726A, 726B with a pre-determined axis of normal function of bone B. The bottom surface of tibial component 704 may also be cemented to a cut-out top surface of bone B to enhance fixation. Floating component 706 is positioned on top of tibial component 704 and its fourth magnetic arrays 748A, 748B are properly aligned with second magnetic arrays 726A, 726B of tibial component 704 to generate second interacting dynamic magnetic fields 780 therebetween. As discussed earlier, the net attractive forces (refer to arrows 780A in the figure) of second interacting dynamic magnetic fields 780 movably couple floating component 706 with tibial component 704. When tibial component 704 is to perform self-centering function, floating component 706 is preferably positioned in its equilibrium or self-centered position on top surface 722 of tibial component 704. Femoral component 702 is placed inside a receiving socket 782A of bone A (or on a precut surface) and its tapered anchor 714 is inserted and affixed to receiving hole 784A mechanically or using cements. The contacting surface of femoral component 702 can also be cemented to a cut-out base of receiving socket 782 as well. Femoral component 702 is preferably aligned with third magnetic arrays 744A, 744B of floating component 706 such that second interacting dynamic magnetic fields 770 coincide with a desirable axis of normal function of bone A.

Continuing with the example of a knee joint as shown in FIG. 8C, advantages of the invention may be further appreciated. When the patient walks or runs, his or her weight compresses first component 702 downwardly toward floating component 706, while the normal reaction force from the ground also pushes second component 704 upwardly toward floating component 706. However, the repulsive forces of first interacting dynamic magnetic fields 770 convert the energy associated with the external forces into magnetic potential energy, dissipating energy transferred to the bone. When the external forces contain shear or rotational components, the attractive forces of second dynamic magnetic fields 780 convert the energy associated with the lateral forces into kinetic energy of floating component 706 and magnetic potential energy of floating component 706 misaligned with first and/or second components 702, 704.

Accordingly, such shear or rotational force is absorbed and/or attenuated and loosening of first and second components 702, 704 from the corresponding bone portions is prevented.

Figure 8D:
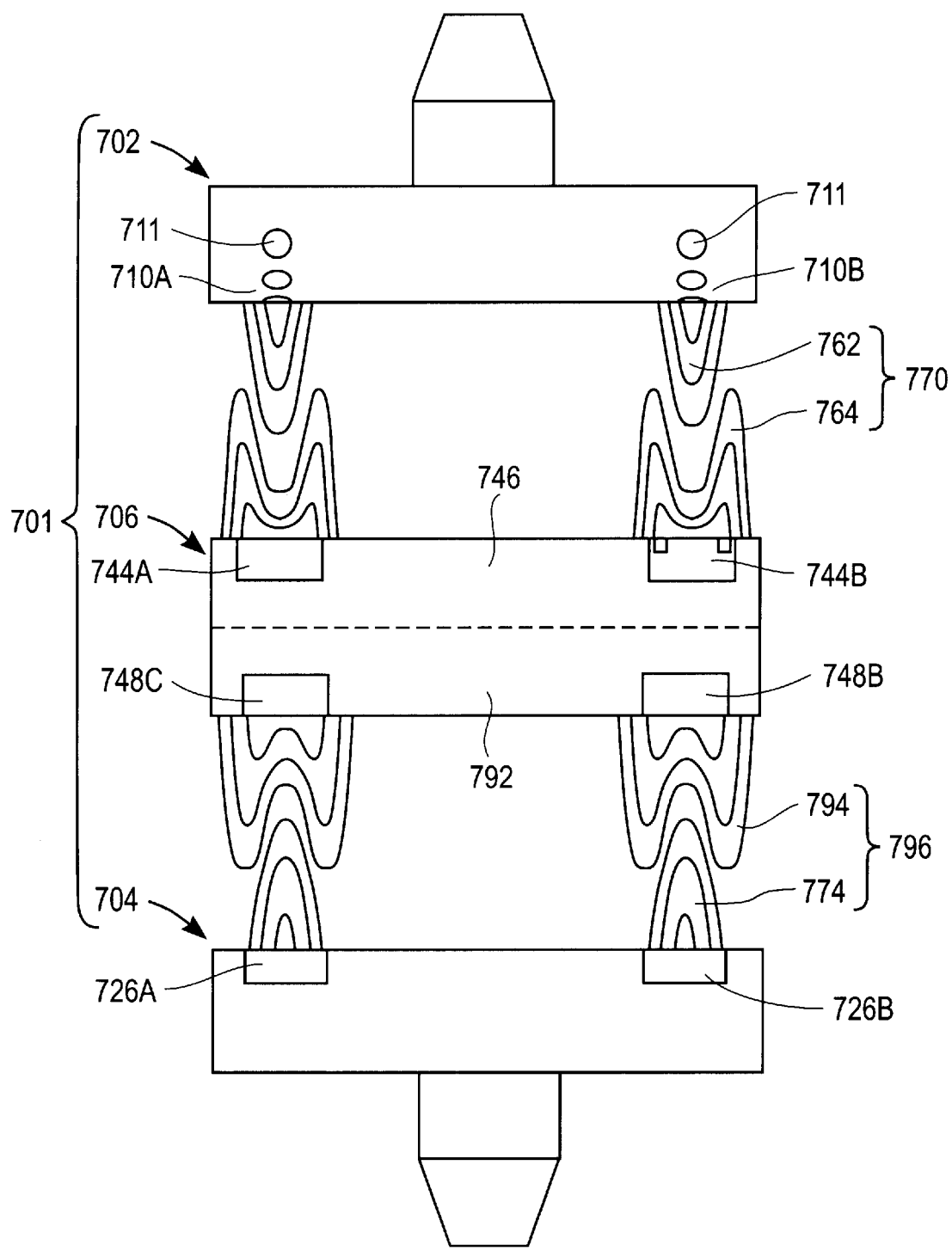
FIG. 8D is a schematic view of exemplary dynamic magnetic fields generated between the securable and floating components of another orthopedic prosthesis according to the present invention.
Figure 8E:
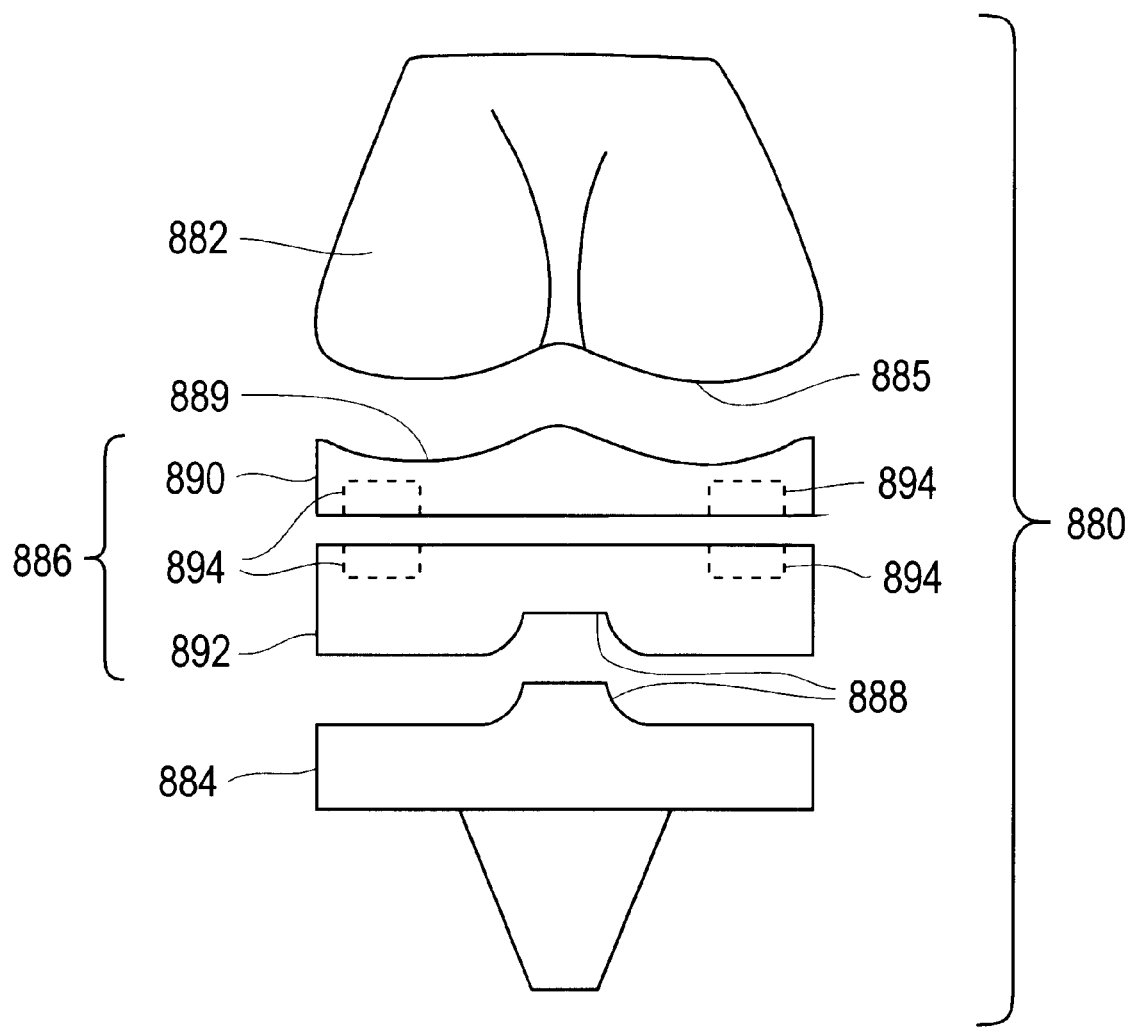
FIG. 8E is a schematic view of an embodiment of the present invention suited for adapting conventional prostheses.

The foregoing orthopedic prosthesis may be modified without departing from the scope of the present invention. For example, the characteristics of the foregoing interacting dynamic magnetic fields may be modified to meet specific medical needs or anatomical requirements of a patient. FIG. 8D is a schematic view of exemplary dynamic magnetic fields generated between the securable and floating components of another orthopedic prosthesis according to the present invention. Such orthopedic prosthesis 701 includes first and second components 702, 704, and upper section 746 of floating component 706 each of which is identical to those of FIGS. 8A and 8B. Lower section 792 of floating component 706, however, is different from that 750 of FIGS. 8A and 8B, in that fourth magnetic arrays 748C, 748D generate another pair of trough-shaped magnetic fields 794 having the same (north) polarity as those 774 of second magnetic arrays 726A, 726B. Therefore, lower section 792 of floating component 706 and second component 704 generate second interacting dynamic magnetic fields 796 which are also characterized by mutually repulsive forces.

Although each section of floating component 706 shown in FIGS. 8A to 8C includes two sets of magnetic arrays (e.g., magnetic arrays 744A and 744B in upper section 746, magnetic arrays 748A and 748B in lower section 750, or 748C and 748D in lower section 792), each section may include a single magnetic array which is functionally equivalent to two or more magnetic arrays and which can generate any of the foregoing composite magnetic fields. Alternatively, the floating component may further include a single magnetic array generating, on its opposing sides, at least two composite magnetic fields defined by identical or different equipotential lines and/or having either polarity. Conversely, the floating component may include more magnetic arrays and/or magnets than shown in FIGS. 8A to 8D and generate desirable composite magnetic fields therearound. As discussed above, it is generally a matter of selection of one of ordinary skill in the relevant art to provide such magnetic arrays and/or magnets thereof capable of generating composite magnetic fields defined by equipotential lines having pre-determined two- or three-dimensional shapes and distribution patterns.

The floating component or securable prosthesis components may be provided with a surface configuration for additional mechanical interaction therebetween. For example, the bottom surface of the first component may have a protruding structure, while the top surface of the floating component may form at least one guide channel capable of receiving such a protruding structure and guiding movement of the first component therealong. This embodiment is beneficial in preventing dislocation of either component when excess external force or shock is exerted on one or both components. It is preferred, however, that the guide channel have a dimension greater than that of the protruding structure so as to prevent constant mechanical contact therebetween and to minimize transmission of the external forces from the first component to the floating component. Similar surface structure may also be provided between the floating and second components.

The floating component may be movably but directly or indirectly attached to the bone portions. For example, the floating component may be connected to one of the first and second components by a flexible element, such as cable, chain, and/or spring to confine movement of the floating component within a pre-selected region. Such embodiment can prevent dislocation of the floating component from excessive external lateral force applied thereupon. Alternatively, at least a portion of the floating component may be retained within the first and/or second components so that movement of the floating component is confined to a region and/or guided along a pre-selected path.

The orthopedic prosthesis of the present invention may also include more than one floating component. One embodiment is to split the floating component of FIGS. 8A through 8D horizontally along the demarcation line between its upper and lower sections and to allow them to operate as separate floating components. Alternatively, an additional floating component may be incorporated to the orthopedic prosthesis of FIGS. 8A to 8D. In a further alternative embodiment, a split floating component may be utilized as shown, for example in FIG. 8E, with an existing conventional implant in order to incorporate advantages associated with the present invention into existing prostheses, whether before or after implantation. Prosthesis 880 includes three basic components, femoral component 882, tibial component 884 and insert 886. Components 882 and 884 may be generally known components, including at least one articulation surface 885 and appropriate securement means 888 for securing the insert component to the prosthesis. As is known in the art, articulation surface 885 bears against and cooperates with the insert to facilitate articulation of the artificial joint. For this reason, the insert is typically made of a high-strength, low-wear material, such as high molecular weight polyethylene. However, according to the present invention, insert 886 comprises first insert portion 890 and second insert portion 892. The two insert portions cooperate through magnetic arrays 894 in the same manner as, for example, the adjacent components of the embodiment of FIG. 8A. Magnetic arrays 894 may be designed in accordance with the teachings of the present invention to address particular disease states or other conditions as required. Upper surface 889 of insert portion 890 is shaped to receive and cooperate with articulation surface 885 femoral component 890, as would the upper surface of a conventional insert. Second insert portion 892 may be secured to lower component 884 through a conventional locking means 888. Insert portions 890 and 892 also may be made of conventional insert materials. Although illustrated in connection with a knee prosthesis, the principles of the invention illustrated in this exemplary embodiment are equally applicable to other joint prostheses. In general, in each of the embodiments shown and described, unless otherwise specifically stated, the cooperating magnetic arrays may be designed by a person of skill in the art to provide magnetic fields that are attractive or repulsive in varying degrees, depending on the condition to be addressed and the desired result to be achieved. Particular illustrations of magnetic fields shown in the drawings and described in the specification are given only as examples to illustrate the principles of the invention.

It will be further appreciated that the orthopedic prosthesis of the present invention may include two floating components each of which is at least partially retained by one of the securable prosthesis components. For example, the floating component may be a piston-like rod which can be inserted inside a cylinder-like chamber of the securable component. By providing various interacting dynamic magnetic fields therebetween, the magnetic rod can be floated inside the chamber and slides vertically therealong. Following illustrates an exemplary embodiment of such prostheses.

Figure 9:
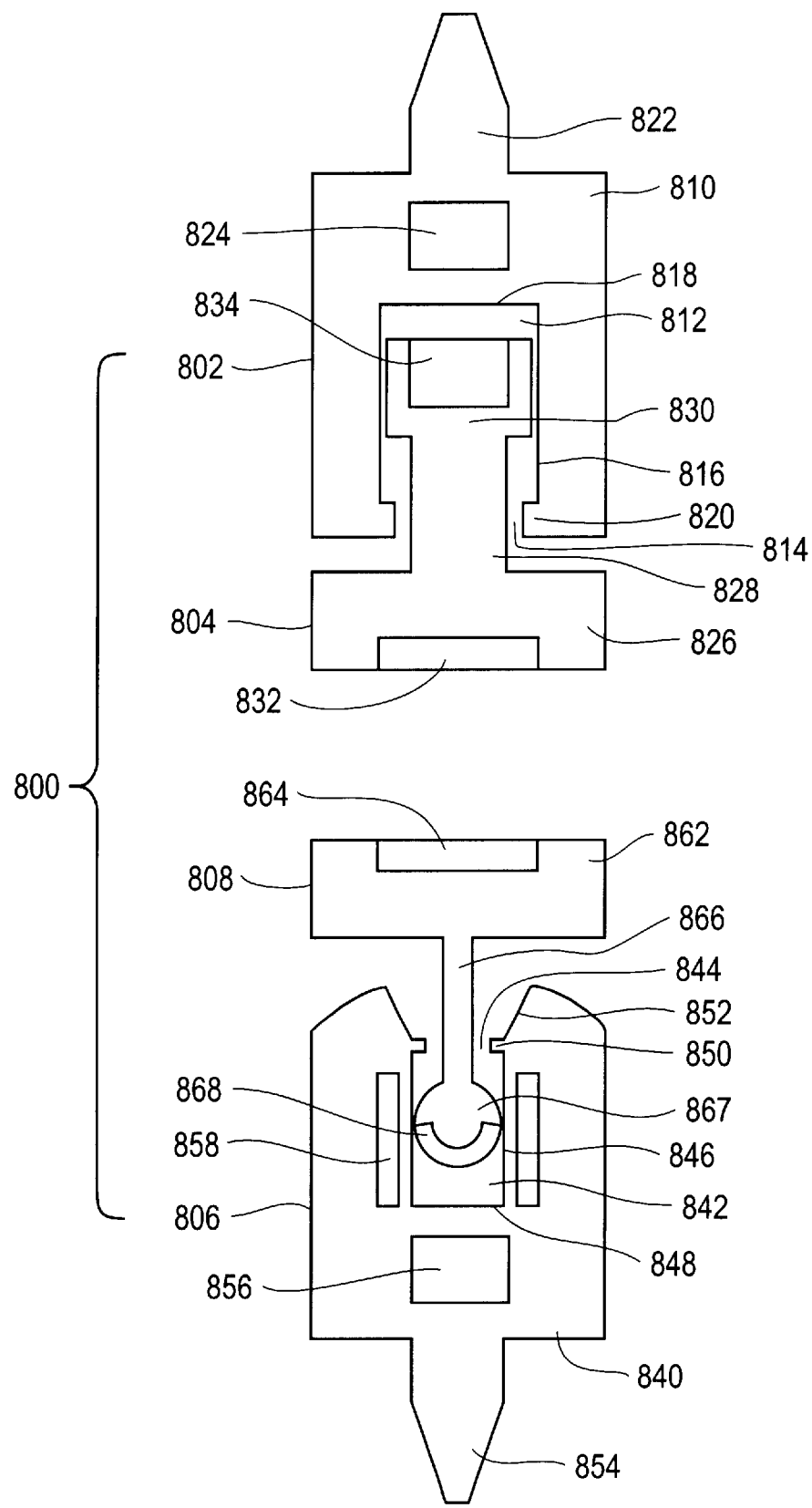
FIG. 9 is a cross-sectional schematic diagram of another exemplary orthopedic prosthesis including multiple floating magnetic components retained by the securable prosthesis components according to the present invention.

FIG. 9 is a cross-sectional schematic diagram of another exemplary orthopedic prosthesis including multiple floating magnetic components retained by the securable prosthesis components according to the present invention. An orthopedic apparatus 800 typically includes a first (prosthesis) component 802, a first floating component 804, a second (prosthesis) component 806, and a second floating component 808. First component 802 is configured to be securable to a first bone portion and to retain at least a portion of first floating component 804. Similarly, second component 806 is also arranged to be securable to a second bone portion and to retain at least a portion of second floating component 808.

First component 802 generally has a cylindrical body 810 and defines a cavity 812 to receive at least a portion of first floating component 804 therein. Cavity 812 is typically cylindrical and defines an inlet opening 814, a side wall 816, and a bottom 818. Along the circumference around inlet opening 814 is provided an annular step 820 which serves as a stopper for excessive displacement of first floating component 804. First component 802 further includes, at its distal end, a tapered anchor 822 shaped and sized to be securable to a receiving socket of the first bone portion. A first magnetic array 824 is also disposed in body 810, preferably between bottom 818 of cavity 812 and tapered anchor 822.

First floating component 804 includes a head 826, a shaft 828, and a base 830. Head 826 includes a first head magnetic array 832 on its top surface. In general, head 826 may have any shape and size, subject to anatomical limitations related to the size and shape of a particular joint. Cylindrical shaft 828 is typically elongated and has a diameter less than that of inlet opening 814 of annular cavity 812 so that shaft 828 can slide vertically through inlet opening 814. Cylindrical base 830 includes a first base magnetic array 834 and has a diameter greater than that of shaft 828 but less than that of annular cavity 812. The diameter of base 830 is also greater than that of annular step 820 so that base 830 cannot be displaced beyond annular step 820.

Second component 806 is generally similar to first component 802, e.g., it has a cylindrical body 840 and defines a cavity 842 with an inlet opening 844, a side wall 846, and a bottom 848. Inlet opening 844 also forms an annular step 850 along its circumference. However, a proximal end 852 of second component 806 is tapered down to annular step 852 to provide space for angular displacement of second floating component 808 therearound. Second component 806 includes a tapered anchor 854 and is provided with a second magnetic array 856. Second component 806 further includes second peripheral magnetic arrays 858 which are disposed adjacent to or on side wall 846 of cylindrical cavity 842 and generates additional composite magnetic fields to further control movement or position of second floating component 808.

Second floating component 808 also includes a head 862 with a second head magnetic array 864 and a cylindrical shaft 866, each of which is substantially similar to that 826, 832, 828 of first floating component 804. Second floating component 808, however, includes a spherical base 867 having a second base magnetic array 868 thereon. Spherical base 866 has a diameter less than that of cylindrical cavity 842 but greater than that of annular step 850. Because spherical base 867 can rotate within annular cavity 842, shaft 844 also rotates around inlet opening 844, thereby enabling second floating component 808 to move vertically as well as to rotate to a certain extent.

Magnetic arrays 824, 832, 834, 856, 858, 864, 868 may have suitable polarity arrangements to effect desirable interacting dynamic magnetic fields therebetween. In an exemplary embodiment, first magnetic array 824 and first base magnetic array 834 may be arranged to generate repulsive forces so that first floating component 804 can float inside cylindrical cavity 812 of first component 802. Second magnetic array 856 and second base and peripheral magnetic arrays 868, 858 are similarly arranged to produce repulsive forces to ensure second floating component 808 to float in cavity 842 of second component 806 as well. Furthermore, first and second head magnetic arrays 832, 864 are also arranged to repel each other.

The magnetic floating components of the present invention may be used with any of the aforementioned resurfacing and/or non-resurfacing magnetic apparatus. For example, the floating component is movably disposed between other magnetic arrays implanted to bone portions. Such floating component may be incorporated into pre-implanted magnetic apparatus to augment, attenuate or modify pre-existing magnetic fields. In the alternative, the floating component and resurfacing or non-resurfacing magnetic apparatus may be provided as a set and implanted together into a joint during a single surgery.

Other variations and modifications of the foregoing orthopedic prostheses and magnetic apparatus are also within the scope of the present invention. The floating component may be made of non-magnetic materials which are transparent to magnetic fluxes emanating from various magnetic arrays of the securable components. Due to the lack of interaction with other magnetic arrays, such a floating component is merely a passive component disposed between the prosthesis components and/or implantable magnetic arrays, and preferably serves as a resurfacing component for such prosthesis and/or apparatus.

Figure 10:
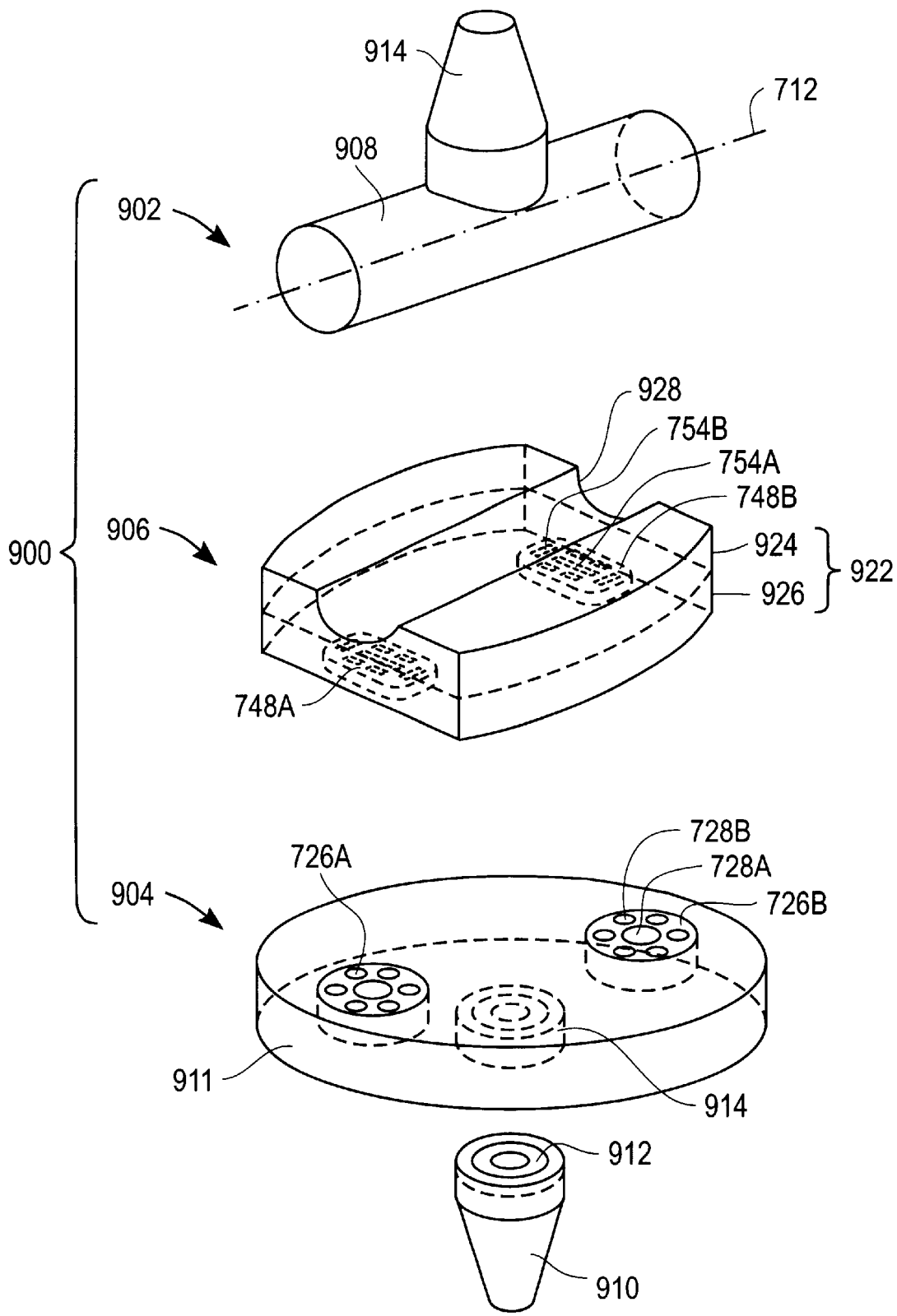
FIG. 10 is a schematic diagram of another exemplary orthopedic prosthesis with a floating component with magnetic arrays according to the present invention.

In the alternative, one of the securable prosthetic components may be made of non-magnetic materials, while the other thereof includes one or more magnetic arrays. FIG. 10 is a schematic diagram of such exemplary orthopedic prosthesis including a magnetic floating component movably disposed between a non-magnetic securable component and a magnetic securable component according to the present invention. Exemplary orthopedic prosthesis 900 includes first component 902 to be secured to a first adjacent bone portion, second component 904 to be secured to a second adjacent bone portion, and a floating component 906 to be movably and/or detachably incorporated between first and second components 902, 904.

As will be appreciated by persons of ordinary skill in the art, the specific configuration of the components will be dictated by factors such as the particular application and patient anatomy. In this exemplary schematic embodiment, first component 902 is shaped and sized substantially as that 702 of FIG. 8A, except that it does not include any magnetic arrays. Second component 904 is also shaped and sized substantially as that 704 of FIG. 8A, but tapered anchor 910 is arranged to be detachable from a body 911 of second component 904. Tapered anchor 910 includes a magnetic array 912 composed of multiple magnets arranged in a concentric pattern with each magnet exposing its first (north) poles upward. Therefore, tapered anchor 910 generates a composite magnetic field defined by bell-shaped equipotential lines. Similarly, body 911 has, in its lower center portion, another magnetic array 914 including multiple magnets arranged in another concentric pattern with their second (south) poles facing downward. Additionally, more than one anchor may be provided with additional magnets. Therefore, magnetic arrays 912, 914 of second component 904 can generate interacting dynamic magnetic field characterized by attractive force therebetween.

Floating component 906 includes body 922 composed of upper section 924 and lower section 926. Lower section 926, similar to lower section 750 of FIGS. 8A to 8D, includes a pair of fourth magnetic arrays 748A, 748B. Upper section 924, however, does not include any magnetic arrays. Rather, upper section 924 is arranged to contact first component 902 and to guide rotational and/or linear translational movement of first component 902 therealong. For example, upper section 924 of FIG. 10 defines a grooved channel 928 shaped and sized to match that of body 908 of first component 902 through mechanical interactions or interferences. Accordingly, first component 902 can rotate along the curved surface of grooved channel 928 of upper section 924 of floating component 906. Such upper section 924 is preferably made of materials, e.g., ultra-high-molecular-weight-polyethylene, which are sheer-resistant and do not tend to produce residue particles due to mechanical friction.

Orthopedic prosthesis 900 of FIG. 10 offers the benefit of incorporating the magnetic floating component of the present invention into conventional orthopedic prostheses. For example, only one component of the conventional prosthesis may be implemented with one or more magnetic arrays and a magnetic floating component may be inserted between the non-magnetic and magnetic securable components of such prosthesis. Accordingly, other portions of such prosthesis can be used without any further modifications.

It is appreciated that second component 904 with detachable tapered anchor 910 offers additional benefit over orthopedic prostheses 700, 701 of FIGS. 8A to 8B. In addition to allow lateral displacement of floating component 906 with respect to second component 904, the embodiment of FIG. 10 further provides an additional mechanism for laterally displacing body 911 of second component 904 over tapered anchor 910 thereof. Accordingly, depending on the application orthopedic prosthesis 900 of FIG. 10 may better absorb, attenuate or dissipate external sheer or rotational forces exerted on various components 902, 904, 906.

It is to be appreciated that, while illustrative embodiments of the invention have been shown and described herein, various changes and adaptions in accordance with the teachings of the present invention will be apparent to those of skill in the art. Such changes and adaptions nevertheless are included within the spirit and scope of the present invention as defined in the following claims.

What is claimed is:

1. An orthopedic prosthesis for treating adjacent bone portions of a joint, comprising:

a first component configured and dimensioned to be secured to a first adjacent bone portion of said joint and including at least one first magnetic array providing a first magnetic field having first predetermined field characteristics;

a second component configured and dimensioned to be secured to a second adjacent bone portion of said joint and including at least one second magnetic array providing a second magnetic field having second predetermined field characteristics; and at least one third component configured and dimensioned to be disposed between said first and second components and including at least two third magnetic arrays each providing a third magnetic field having third predetermined field characteristics, said third magnetic arrays disposed on different sides of said third component;

wherein said first, second, and third predetermined field characteristics are selected to interact such that said first, second, and third magnetic arrays cooperate to urge said adjacent bone portions of said joint into predetermined desired relationship and to constrain relative motion between said adjacent bone portions in at least two dimensions.

2. The prosthesis according to claim 1, wherein said relative motion is at least one of rotation, flexion and extension of said adjacent bone portions.

3. The prosthesis according to claim 1, wherein:

said at least one third component comprises separate upper and lower portions, said portions further having at least fourth and fifth cooperating magnetic arrays, respectively; and said fourth magnetic array is disposed in opposition to said fifth magnetic array such that relative motion between said upper and lower portions is constrained thereby.

4. The prosthesis according to claim 1, wherein each of said first, second, and third magnetic arrays comprises at least one magnet configured and dimensioned to provide a first, second, and third composite magnetic field having said predetermined first, second, and third field characteristics, respectively.

5. The prosthesis according to claim 4, wherein;

said first and third composite magnetic fields generate repulsive force therebetween; and said second and third composite magnetic fields generate attractive force therebetween.

6. The prosthesis according to claim 4, wherein;

said first and third composite magnetic fields generate a first repulsive force therebetween; and said second and third composite magnetic fields generate a second repulsive force therebetween.

7. The prosthesis according to claim 4, wherein at least one of said composite magnetic fields is asymmetrical.

8. The prosthesis according to claim 1, wherein:

said first predetermined field characteristics comprise magnetic equipotential lines forming at least one first peak;

said third predetermined field characteristics comprise magnetic equipotential lines forming at least two third peaks; and said first magnetic array and one of said third magnetic arrays are positioned with respect to each other such that said first peak is movably disposed between said at least two third peaks.

9. The prosthesis according to claim 1, wherein:

said first predetermined field characteristics comprise magnetic equipotential lines forming at least one first peak;

said third predetermined field characteristics comprise magnetic equipotential lines forming a loop of third peaks; and said first magnetic array and one of said third magnetic arrays are positioned with respect to each other such that said first peak is movably disposed within said loop of said third peaks.

10. The prosthesis according to claim 1, wherein:

said first predetermined field characteristics comprise magnetic equipotential lines forming a first loop of first peaks;

said third predetermined field characteristics comprise magnetic equipotential lines forming a third loop of third peaks; and said first magnetic array and one of said third magnetic arrays are positioned with respect to each other such that said first loop of said first peaks is movably disposed within said third loop of said third peaks.

11. The prosthesis according to claim 1, wherein said first component includes a body having a upper first magnetic array and an anchor having a lower first magnetic array, said anchor configured and dimensioned to be secured to said first adjacent bone portion of said joint and said upper and lower first magnetic arrays are configured to generate attractive force therebetween to secure together said body and anchor.

12. The prosthesis according to claim 1, further comprising a flexible element linking at least one of the first and second components with the third component.

13. The prosthesis according to claim 1, wherein:
   at least one of said first and second components defines a cavity, with at least one magnetic array disposed at a bottom portion of the cavity; and
   said third component includes a shaft portion configured and dimensioned to be slidingly received in said cavity, with at least one magnetic array disposed on said shaft in opposition to said magnetic array at the bottom of the cavity.

14. The prosthesis according to claim 13, wherein said magnetic array disposed at the bottom of the cavity and said magnetic array disposed on said shaft cooperate to provide a mutual repulsive force to absorb shocks transmitted through said components.

15. An orthopedic prosthesis for treating adjacent bone portions of a joint, comprising:
   a first component configured and dimensioned to be secured to a first adjacent bone portion of said joint and including at least one first magnetic array providing a first magnetic field having first predetermined field characteristics;
   a second component configured and dimensioned to be secured to a second adjacent bone portion of said joint and including at least one second magnetic array providing a second magnetic field having second predetermined field characteristics;
   a third component configured and dimensioned to be disposed between said first and second components and including at least one third magnetic array providing a third magnetic field having third predetermined field characteristics; and
   a fourth component configured and dimensioned to be movably disposed between said third and second components and including at least one fourth magnetic array providing a fourth magnetic field having fourth predetermined field characteristics;
   wherein said first, second, third, and fourth predetermined field characteristics are selected to interact such that said first, second, third, and fourth magnetic arrays cooperate to urge said adjacent bone portions of said joint into predetermined desired relationship and to constrain relative motion between said adjacent bone portions in at least two dimensions.

16. An orthopedic prosthesis for treating adjacent bone portions of a joint, comprising:
   a first component configured and dimensioned to be secured to a first adjacent bone portion of said joint and including at least one first magnetic array providing a first magnetic field having first predetermined field characteristics;
   a second component configured and dimensioned to be secured to a second adjacent bone portion of said joint; and
   at least one third component configured and dimensioned to be movably disposed between said first and second components and including at least one third magnetic array providing a third magnetic field having third predetermined field characteristics;
   wherein said first and third predetermined field characteristics are selected to interact such that said first and third magnetic arrays cooperate to urge said adjacent bone portions of said joint into predetermined desired relationship and to constrain relative motion between said adjacent bone portions in at least two dimensions.

17. An orthopedic prosthesis for treating a joint, comprising:
   a first component configured and dimensioned to be secured to a first bone of the joint;
   a second component configured and dimensioned to be secured to a second bone of the joint; and
   an insert member disposed between the first and second components, said member being secured to one said component and bearing against the opposite component, wherein
      said insert member comprises separate first and second portions with cooperating magnetic arrays, and
      said magnetic arrays constrain relative motion between said first and second portions.

18. The prosthesis according to claim 17, wherein:
   the first component has an articulation surface configured to facilitate joint articulation; and
   the first portion of the insert member has a surface configured to receive and cooperate with said articulation surface.

19. The prosthesis according to claim 17, wherein said cooperating magnetic arrays exhibit attractive forces with respect to one another.

20. The prosthesis according to claim 17, wherein said cooperating magnetic arrays exhibit a combination of attractive and repulsive forces with respect to one another.

* * * * *